US011064957B2

(12) United States Patent
Martin

(10) Patent No.: US 11,064,957 B2
(45) Date of Patent: *Jul. 20, 2021

(54) DENTAL IMAGER AND METHOD FOR RECORDING PHOTOGRAPHIC IMPRESSIONS

(71) Applicant: Marco Martin, Saint Helena, CA (US)

(72) Inventor: Marco Martin, Saint Helena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/773,733

(22) Filed: Jan. 27, 2020

(65) Prior Publication Data

US 2020/0155087 A1 May 21, 2020

Related U.S. Application Data

(63) Continuation of application No. 15/422,201, filed on Feb. 1, 2017, now Pat. No. 10,542,946.
(Continued)

(51) Int. Cl.
*A61B 6/14* (2006.01)
*A61B 1/00* (2006.01)
(Continued)

(52) U.S. Cl.
CPC ............ *A61B 6/14* (2013.01); *A61B 1/00149* (2013.01); *A61B 1/00172* (2013.01); *A61B 1/05* (2013.01);
(Continued)

(58) Field of Classification Search
CPC .......... A61C 3/00; A61C 11/00; A61C 11/02; A61C 11/06; A61C 13/00; A61C 13/04; A61C 13/06; A61B 1/00; A61B 1/00064; A61B 1/00066; A61B 1/00071; A61B 1/0008; A61B 1/00087; A61B 1/00096; A61B 1/00131; A61B 1/0014; A61B 1/00147; A61B 1/00149; A61B 1/0016;
(Continued)

(56) References Cited

U.S. PATENT DOCUMENTS 6,276,933 B1 8/2001 Melnyk
6,371,909 B1 4/2002 Hoeg
(Continued)

FOREIGN PATENT DOCUMENTS

DE 102006041020 A1 3/2005
JP 2011-050441 A 3/2011
(Continued)

*Primary Examiner* — Anastasia Midkiff
(74) *Attorney, Agent, or Firm* — Lowry Blixseth APC; Scott M. Lowry

(57) ABSTRACT

A dental imager includes an elongated handle with a rotatable head coupled to a distal end thereof and having a central platform with a plurality of arcuate scanning arms pivotally coupled thereto by a hinge. The arcuate scanning arms are of a shape and size for general deployment around a tooth and each include at least one scanner and a roller guide that comfortably rolls along the surface of the tooth or gums to bias the scanners a desired distance from the surface of the tooth, conducive for imaging thereof. In this respect, such a dental imager may be used in a process to scan and record the contours of an intraoral surface, the data of which may be used to create a digital three-dimensional surface impression printable by a 3D printer or the like.

31 Claims, 8 Drawing Sheets

Related U.S. Application Data

(60) Provisional application No. 62/289,504, filed on Feb. 1, 2016.

(51) Int. Cl.
   *A61B 5/00* (2006.01)
   *A61B 1/05* (2006.01)
   *A61B 90/50* (2016.01)
   *A61C 9/00* (2006.01)
   *A61B 1/247* (2006.01)
   *A61B 1/24* (2006.01)
   *A61B 5/145* (2006.01)

(52) U.S. Cl.
   CPC ............ *A61B 5/0088* (2013.01); *A61B 5/682* (2013.01); *A61B 5/6835* (2013.01); *A61B 5/6844* (2013.01); *A61B 90/50* (2016.02); *A61C 9/008* (2013.01); *A61B 1/00101* (2013.01); *A61B 1/00147* (2013.01); *A61B 1/24* (2013.01); *A61B 1/247* (2013.01); *A61B 5/0062* (2013.01); *A61B 5/14542* (2013.01); *A61B 5/45* (2013.01); *A61B 5/4547* (2013.01); *A61B 2560/0406* (2013.01); *A61C 9/0053* (2013.01)

(58) Field of Classification Search
   CPC ............ A61B 1/00163; A61B 1/00172; A61B 1/00174; A61B 1/00181; A61B 1/08; A61B 1/042; A61B 1/045; A61B 1/05; A61B 1/06; A61B 1/0661; A61B 1/0676; A61B 1/0692; A61B 1/24; A61B 1/247; A61B 2090/033; A61B 2090/034; A61B 2090/036; A61B 2090/3612; A61B 5/00; A61B 5/0059; A61B 5/0062; A61B 5/0073; A61B 5/0082; A61B 5/0088; A61B 5/45; A61B 5/4538; A61B 5/4547; A61B 5/4552; A61B 5/4557; A61B 5/68; A61B 5/6801; A61B 5/6813; A61B 5/682; A61B 5/683; A61B 5/6831; A61B 5/6835; A61B 5/6843; A61B 5/6844; A61B 2562/16; A61B 2562/22; A61B 6/00; A61B 6/08; A61B 6/10; A61B 6/14; A61B 6/145; A61B 6/44; A61B 6/4405; A61B 6/4411; A61B 6/4429; A61B 6/50; A61B 6/505; A61B 6/587; A61B 6/589; A61B 17/24; A61B 90/00; A61B 90/03; A61B 90/36; A61B 90/361; A61B 90/376; A61B 90/50; A61B 2560/00; A61B 2560/04; A61B 2560/0406; A61B 2560/0443; A61B 2560/0462
   See application file for complete search history.

(56) References Cited

U.S. PATENT DOCUMENTS 7,374,533 B2  5/2008 Hoeg
10,542,946 B2 * 1/2020 Martin ............... A61B 1/00149

FOREIGN PATENT DOCUMENTS

| RU | 2571449 | 12/2015 |
| WO | WO2012149453 | 11/2012 |
| WO | WO 2015/188286 | 12/2015 |

* cited by examiner

DENTAL IMAGER AND METHOD FOR RECORDING PHOTOGRAPHIC IMPRESSIONS

BACKGROUND OF THE INVENTION

The present invention generally relates to a dental imager and related method for collecting digital impressions. More specifically, the present invention relates to a dental imager in the form of a hand-manipulatable scanner that digitally records three-dimensional images of the contours and surfaces of the oral cavity when biased away and passed over teeth.

A dental impression is a reproduction of an oral cavity. Dentists, orthodontists, and dental practitioners collect dental impressions for a variety of reasons, such as making removable dentures, making and installing dental crowns, creating a dental bridge, repairing installed dentures, making a mouth guard or customized enamel whitening tray, creating models for diagnostic study, or manufacturing and installing other oral appliances, etc.

Currently, trained practitioners can take dental impressions by creating a solid mold of the oral cavity. The process requires filling a "U" shaped plastic tray with a hardening chemical paste that is then pushed up and around the entire dental arc of the patient. The paste hardens into an impression body, creating a negative relief of the mouth of the patient. A durable mold can then be created using the negative space of the impression body. This form of recording dental impressions presents numerous limitations and inconveniences.

For example, the chemical paste used to create the impression must solidify when applied to the dental arc of a patient. The solidification process may be an uncomfortable experience for patients who remain in a reclined position with their mouth open for a prolonged period of time (e.g., six to ten minutes). Moreover, the chemical paste generates excessive salivation during the impression curing process, which can limit the ability of the patient to breathe properly, especially when reclined. The removal of the cured dental impression can also be an uncomfortable experience for the patient, even when done properly. Discomfort is compounded by the fact that chemical pastes used to create the dental impression may leave a bad taste in the mouth, even after removal, as residues of the paste get stuck in the cracks of the teeth.

Moreover, the physical impression is typically unable to capture every indentation, crack, or protuberance of the oral cavity. For example, if the patient has attachments on the surface of their teeth, including braces or permanent retainers, the entire process is compromised and it may not be possible to create a physical dental impression. This is because the attachments unavoidably jeopardize the accuracy and integrity of the impression during the curing and removal steps. Moreover, the inability to prevent scratching of the cured chemical paste mold sometimes results in the undesirable need to re-take the dental impressions (i.e., re-do the mold).

The nature, consistency, and malleability of physical dental impression bodies also make taking a targeted impression of only a limited area within the oral cavity extremely difficult, if not impossible. Thus, skilled practitioners typically make an impression of the entire dental arc, even if the patient only requires treatment on a single tooth or area of the oral cavity. Creating dental impressions with an impression and mold also creates excessive waste from both the impression curing process and the creation of the durable resulting mold. Of course, this also means that practitioners must continually purchase the consumables needed to make the impressions and molds.

Creating physical dental impressions may also be time consuming and labor intensive. For example, after the "U"-shaped plastic tray with the chemical paste is pushed up and around the entire dental arc of the patient, the practitioner must wait for the chemical paste to cure. Thereafter, the practitioner must wait upwards of several hours for the dental stone material poured into the casting formed by the cured chemical paste to cure or solidify. Personnel must also be highly trained to take physical dental impressions using the current impression body and mold method, as it is easy to improperly: (a) mix the chemical paste; (b) apply the chemical paste to the "U"-shaped tray; (c) insert the tray into the mouth; (d) wait an insufficient duration for the dental impression to cure; (e) remove the tray once the impression cures; or (f) create a mold from the cured dental impression. Inadequately trained and especially inexperienced personnel inevitably need to take multiple dental impressions of the same patient in one sitting, until a proper mold has been generated. This is undesirable for the patient and practitioner.

Over the course of the last thirteen years, several technologies have been produced to try and introduce a better way of taking dental impressions, such as by scanning the dental arc and creating a 3D digital model. Some systems disclosed in the prior art incorporate light-based scanning systems to create a three-dimensional digital representation of the oral cavity. In this respect, some systems are designed to mimic the "U"-shape dental trays in the form of a scanner, but those too include limitations regarding the wide scanning area and the amount of data gathered. For example, instead of targeting just the teeth, these scanners record significant portions of the gums, and some portions of the upper roof and lower bottom of the mouth. As a result, the 3D scanned digital impressions must be subject to a higher amount of digital work and adjustment via computer software, to be ready for 3D or casting of the mold by the dentist. Moreover, the "U"-shaped dental scanners are also unable to efficiently take an impression of a single tooth or selected area of the mouth given that the "U"-shaped tray necessitates scanning the entire dental arc, thereby inherently including the same limitations as current methods related to "U"-shaped trays that utilize chemical paste. While these systems may be designed to replace curing chemical pastes with digital scanners, such systems are not necessarily significantly more efficient.

For example, U.S. Publication No. 2012/0064477 to Schmitt, the contents of which are herein incorporated by reference in their entirety, discloses a dental impression tray that includes a deformable impression compound therein for obtaining a dental impression. One or more sensors may be positioned to identify changes in the deformable impression compound when taking an impression of the oral cavity. The sensors may identify different arrangements, shapes, and/or dimensions and relay such information to a processor to create a digital representation of the oral cavity. In this example, the deformable impression compound is disposed within the interior of a "U"-shaped tray and closely resembles the chemical-curing trays traditionally used for creating dental impression molds.

In another example, U.S. Pat. No. 6,976,841 to Osterwalder, the contents of which are herein incorporated by reference in their entirety, discloses an intra-oral dental irradiation imager that uses a number of scanners arranged in a "U"-shaped tray to harden material therein, similar to the chemical trays used for generating whole dental-arc impression bodies. In making dental impressions, the device projects light in a spectrum that functions as a catalyst to harden material within the "U"-shaped tray, similar to the traditional process of creating physically-cured dental impression molds. The scanners are arranged throughout the "U"-shaped tray to harden the dental impression material when inserted over the teeth of the patient.

U.S. Pat. No. 6,386,867 to Durbin, the contents of which are herein incorporated by reference in their entirety, discloses a "U"-shaped mouthpiece with a camera permanently attached to a fixed "U"-shaped track. The camera slides to a plurality of predetermined positions along the fixed curved track to capture images of the dental structure within the oral cavity. An air-directing nozzle is movably coupled with the camera along the "U"-shaped track to ensure that the tooth-gum interface is free from unwanted debris during imaging.

U.S. Publication No. 2005/0202363 also to Osterwalder, the contents of which are herein incorporated by reference in their entirety, discloses a "U"-shaped dental tray similar in structure to chemical trays used for making traditional physical dental impression molds, but with a plurality of LED lights fixed on an interior surface thereof, and a plurality of imaging sensors fixed on an opposite interior surface thereof. The LED lights and the imagining sensors are not moveable. In this respect, light emitted from the LEDs is refracted by the teeth situated between the LEDs and the sensors. The sensors capture and record an image of the teeth based on the light passing therethrough. Although, illumination and recordation of translucent oral objects does not allow for readily-available surface mapping, as the light passes through the object before being recorded, rather than bouncing off the object. Consequently, it is not possible to image completely opaque objects.

U.S. Publication No. 2015/0079534 to Tsuji, the contents of which are herein incorporated by reference in their entirety, discloses a "U"-shaped tray containing patterned light projectors and imaging sensors. The tray is used to take three-dimensional intraoral images of teeth by activating the light projectors within the interior surface of the "U"-shaped tray and recording the intersection of the light patterns using the installed sensors. The sensors and projectors are set in fixed positions within the tray.

In other known digital impression systems, light-based scanners are implemented as part of a hand-held tool that can be freely maneuvered around the oral cavity to collect digital impressions. For example, U.S. Pat. No. 8,520,925 to Duret, the contents of which are herein incorporated by reference in their entirety, discloses a hand-held sensor wand for taking three-dimensional color imprints of surfaces. The sensor wand houses a set of at least two CCD or CMOS color sensors, in fixed positions in the wand base, and can be positioned over an area to collect a digital image. Although, without proper guides, it is difficult to achieve the correct shape and distances being scanned. Moreover, such a wand increases the potential for accidental scans of the tongue and other parts of the mouth, thereby decreasing the accuracy of the scans and/or requiring user training to ensure an accurate the 3D model is produced.

Despite addressing some of the problems associated with physical dental impression molds, known digital impression systems include drawbacks. For example, "U"-shaped scanner arrays and "U"-shaped tracks with movable scanners are limited by size and are not always able to fit every oral cavity size. This can present an issue, for example, when trying to scan the mouth of a child when using a device sized to scan an adult mouth. Practitioners would need to purchase a variety of differently-sized devices to cater to all patients. This means a large initial expense for equipment, thus inhibiting the potential cost advantage of foregoing the consumables needed to create physical dental impression bodies and molds.

The unconstrained nature of current hand-held scanning systems may require additional training so the practitioner understands how to obtain accurate images since a guide is notably absent. Furthermore, the practitioner must have a steady hand to ensure the accuracy of the images, depending on what is being imaged. For example, the practitioner must ensure that proper focal distances are maintained while scanning, and that the imaging sensor does not touch the surface being examined. These limitations can result in digital representations of the oral cavity that need correction or post-processing before being usable, thereby increasing time and cost for producing a dental impression.

There exists, therefore, a significant need in the art for a low cost adaptable dental imager that can record detailed three-dimensional representations of oral cavity surfaces, without needing cumbersome trays, expensive consumable products, or a trained and skilled user. The present invention fulfills these needs and provides further related advantages.

SUMMARY OF THE INVENTION

One embodiment of a dental imager for imaging an intraoral cavity as disclosed herein includes an elongated handle having a proximal end and a distal end. A head at the distal end of the elongated handle may have a size and shape for select insertion into the intraoral cavity, while holding the dental imager at the opposite proximal end. In this respect, the elongated handle may include a rubber grip at the proximal end and be of a length of about 5-6 inches. The dental imager may also include at least one lateral scanning arm projecting outwardly from the head of the elongated handle and have a scanner associated therewith for imaging at least a portion of the intraoral cavity. The scanner may generally project inwardly so as to align and image teeth or other intraoral features. Additionally, the dental imager may include a guide having a size and shape for substantial continuous engagement with the intraoral cavity while simultaneously substantially biasing the scanner at a relatively consistent distance from the intraoral cavity as the dental imager moves relative to the intraoral cavity during imaging. In this respect, the guide may help position the scanner at a preferred location relative to the tooth surface or gums to enhance image quality by substantially reducing errors related to select positioning of the dental imager from the tooth or other imaged portion of the intraoral cavity.

In another aspect of this embodiment, the at least one lateral scanning arm may include a pair of arcuate lateral scanning arms that couple to the head opposite one another. Here, each of the pair of arcuate lateral scanning arms may include a top scanner and a bottom scanner. One of the top scanners or the bottom scanners may mount to the pair of arcuate lateral scanning arms at an angle between 30 and 60 degrees, while the other of the top scanners or the bottom scanners may mount to the pair of arcuate lateral scanning arms at an angle between 120 and 180 degrees, to better maximize scanning coverage. In some aspects, the scanning coverage of the top and bottom scanners may substantially or partially overlap. In another aspect of this embodiment, the dental imager may include an activation sensor that includes an emitter in one of the pair of arcuate lateral scanning arms and a detector in the other of the pair of arcuate lateral scanning arms. Here, the emitter and the detector may be generally aligned such that a beam generated by the emitter is receivable by the detector during non-use and generally blocked by the intraoral cavity during use of the dental imager. In this respect, the pair of arcuate lateral scanning arms may be offset from one another by a distance that allows for slide-in engagement of the dental imager over one or more teeth. That is, each of the arcuate lateral scanning arms may generally encompass the outer lateral surfaces of one or more teeth, while the head encloses the top surface thereof. Additionally, the head may pivot relative to the elongated handle by way of a handle bellow or a ball joint and otherwise be exchangeable with the elongated handle in the event one head is preferred to another head for scanning purposes or otherwise.

In one embodiment, the head may include a rotating head that couples to the distal end of the elongated handle by a ball joint. Such connection may permit simultaneous longitudinal, lateral, and/or vertical 360 degree movement of the head relative to the elongated handle. In another aspect of this embodiment, the rotating head may further include a platform having at least one lateral scanning arm, or the pair of lateral scanning arms, coupled thereto.

The guide may include a roller rotatably coupled to the head and configured to provide rolling support for the dental imager over the intraoral cavity. Alternatively or in addition to, the guide may be a pad having a surface permitting sliding movement over the intraoral cavity. In these embodiments, the guide may couple directly to the head and generally traverse the top surface of the teeth during scanning. In this respect, the head may also include at least one central scanner mounted therein and having a height relatively less than the roller or the pad to bias the central scanner up and away from a top surface of the teeth to enhance scanning thereof.

In another aspect of these embodiments, the at least one lateral scanning arm, or the pair of lateral scanning arms, may couple to the head via a flexible coupling. Here, the flexible coupling may permit the lateral scanning arm(s) to move relative to the head and/or elongated handle while simultaneously maintaining contact with the outer surface of the teeth, such as by way of the aforementioned guides. This may be beneficial in that the scanners can generally track the curvature of the teeth during scanning. A compass or other positional sensor within the lateral scanning arm(s) may track the angular orientation of its respective lateral scanning arm as the lateral scanning arm moves about the flexible coupling. In some embodiments, the flexible coupling may include a spring, a hinge, an accordion-shaped bellow, or a ball joint, each of which generally medially bias the respective lateral scanning arm into engagement with the teeth. In this respect, the guide may include a lateral roller guide or a lateral pad coupled to one end of each of the lateral scanning arm(s) at an angle of about 30-45 degrees relative thereto, for contact with the intraoral cavity. More specifically, the lateral roller guide may couple about an axis formed to an interior of the lateral scanning arm.

In another aspect, these embodiments may include a front medial scanning arm and a rear medial scanning arm coupled to the head. The scanning arms may couple to the head by a hinge, a spring, a resilient elastic material, a multi-axial pivot, or a ball joint. Additionally, the head may include a front angled platform carrying a front scanner at an angle between 30 and 60 degrees and a rear angled platform carrying a rear scanner at an angle between 30 and 60 degrees. Here, the guide may include a front pad coupled to the front angled platform above the front scanner and a rear pad coupled to the rear angled platform above the rear scanner. As above, the guides may selectively bias the head of the dental scanner from a top surface of the teeth during scanning such that the front and rear scanners may better maximize imaging of the top of the teeth.

The dental imager may also include a communication circuit integral with the elongated handle and in communication with the at least one scanner for selectively transmitting imaging data of the intraoral cavity. The communication circuit may include a wireless transmitter, a USB connector, or a fiber optic connector. The scanner may be selected from the group consisting of a time of flight (ToF) scanner, a stereoscopic vision scanner, a light field moment imaging scanner, a fixed structured light scanner, a programmable structured light (DLP) scanner, a 3D or 4D ultrasound scanner, a digital camera scanner, a light emitting diode (LED) scanner, and a laser scanner.

In another embodiment, a front pad and a rear pad may mount to the head, wherein the at least one lateral scanning arm includes a pair of static scanning arms immovably coupled to the head. Here, each of the static lateral scanning arms may include one or more of the scanners for imaging the intraoral cavity.

In another embodiment as disclosed herein, the dental imager for imaging an intraoral cavity may include an elongated handle having a proximal end and a distal end, a head at the distal end of the elongated handle and having a size and shape for select insertion into the intraoral cavity, and a pair of arcuate lateral scanning arms flexibly coupled to the head and generally projecting outwardly opposite one another, each having a scanner associated therewith for imaging at least a portion of the intraoral cavity. A central roller may rotatably couple to the head and be configured to provide rolling support for the dental imager over the intraoral cavity. Additionally, a lateral roller guide may couple to each of the pair of arcuate lateral scanning arms at an angle of about 30-45 degrees relative thereto. Here, each of the central roller and the lateral roller guides may have a size and shape for substantial continuous engagement with the intraoral cavity (e.g., teeth) while simultaneously substantially biasing the scanners at a relatively consistent distance from the intraoral cavity as the dental imager moves relative to the intraoral cavity during imaging.

Each scanner may include a top scanner and a bottom scanner such that one of the top scanners or the bottom scanners mount to the arcuate lateral scanning arms at an angle between 30 and 60 degrees and the other of the top scanners or the bottom scanners mount to the arcuate lateral scanning arms at an angle between 120 and 180 degrees to enhance scanning coverage. Additionally, the dental scanner may also include at least one central scanner mounted to the head having a height relatively less than the central roller.

The dental scanner as disclosed in these embodiments may also include an activation sensor such as an emitter in one of the pair of arcuate lateral scanning arms and a detector in the other of the pair of arcuate lateral scanning arms, the emitter and the detector being generally aligned such that a beam generated by the emitter is receivable by the detector during non-use and generally blocked by the intraoral cavity (e.g., one or more teeth) during use. Here, the head may include a rotating head having a platform with the pair of arcuate lateral scanning arms coupled thereto. Additionally, the head may couple to the distal end of the elongated handle by a ball joint permitting simultaneous longitudinal, lateral, and/or vertical 360 degree movement relative thereto.

Each of the pair of arcuate lateral scanning arms may include a compass tracking its angular orientation, wherein each of the pair of arcuate lateral scanning arms may be moveable by way of coupling to the head that includes a spring, a hinge, an accordion-shaped bellow, or a ball joint, each of which generally inwardly bias the at least one lateral scanning arm for proximal placement near the scanned surface of the intraoral cavity.

A communication circuit may be integral with the elongated handle and in communication with the scanners for selectively transmitting imaging data of the intraoral cavity, wherein the head may include a front angled platform carrying a front scanner at an angle between 30 and 60 degrees and a rear angled platform carrying a rear scanner at an angle between 30 and 60 degrees. Additionally, the dental scanner in this embodiment may also include a front medial scanning arm and a rear medial scanning arm coupled to the head. Here, the head may pivot relative to the elongated handle by way of a handle bellow or a ball joint. Each of the lateral roller guides may couple about an axis formed to an interior of the respective arcuate lateral scanning arm.

In another embodiment of a dental imager for imaging an intraoral cavity as disclosed herein, an elongated handle may have a proximal end and a distal end with a head at the distal end thereof and pivotable relative to the elongated handle by way of a handle bellow or a ball joint. The head may have a size and shape for select insertion into the intraoral cavity for purposes of scanning teeth and/or gums. In this respect, a pair of flexible lateral scanning arms may be positioned generally opposite one another by a distance sufficient to generally encompass the other surface of one or more teeth. The flexible lateral scanning arms may be associated with the head of the elongated handle and each may include a scanner associated therewith for imaging at least a portion of the intraoral cavity. Each flexible lateral scanning arm may also include a compass for tracking the angular orientation thereof as the flexible scanning arms moves or flexes relative to the intraoral cavity (e.g., over the contoured tooth surface) during scanning. The dental imager may also include at least one central scanner mounted to the head and having a height relatively less than a medial pad therein, wherein each of the pair of flexible lateral scanning arms includes a top scanner and a bottom scanner to maximize scanning coverage. Additionally, the lateral pad may couple to each of the pair of flexible lateral scanning arms at an angle of about 30-45 degrees relative thereto.

In another aspect of this embodiment, a medial pad coupled to the head may be configured to provide sliding support for the dental imager over the intraoral cavity, wherein the lateral pads and the medial pad may have a size and shape for substantial continuous engagement with the intraoral cavity while simultaneously substantially biasing the scanners at a relatively consistent distance from the intraoral cavity as the dental imager moves relative to the intraoral cavity during imaging. To provide enhanced scanning coverage, the dental imager of this embodiment may also include a front medial scanning arm and a rear medial scanning arm coupled to the head. The flexible lateral scanning arms and/or the front medial scanning arm and/or the rear medial scanning arm may couple to the head by a hinge, a spring, a resilient elastic material, a multi-axial pivot, or a ball joint and the head may include a front angled platform carrying a front scanner at an angle between 30 and 60 degrees and a rear angled platform carrying a rear scanner at an angle between 30 and 60 degrees.

Additionally, in another aspect of these embodiments, the dental scanner may include an activation sensor that includes an emitter in one of the pair of flexible lateral scanning arms and a detector in the other of the pair of flexible lateral scanning arms. The emitter and the detector may be generally aligned such that a beam generated by the emitter is receivable by the detector during non-use, i.e., when no object such as teeth block transmission, and generally blocked by the intraoral cavity or teeth during use, i.e., when the dental imager generally encompasses one or more teeth during scanning. One of the top scanners or the bottom scanners may mount to the pair of flexible lateral scanning arms at an angle between 30 and 60 degrees and the other of the top scanners or the bottom scanners may mount to the pair of flexible lateral scanning arms at an angle between 120 and 180 degrees. Additionally, a front pad may couple to the front angled platform above the front scanner and a rear pad may couple to the rear angled platform above the rear scanner, wherein the head pivots relative to the elongated handle by way of a handle bellow or a ball joint. The dental imager may also include a communication circuit that includes a wireless transmitter, a USB connector, or a fiber optic connector integral with the elongated handle and in communication with the scanners selectively transmitting imaging data of the intraoral cavity, wherein the head is exchangeable with the elongated handle.

In another embodiment, a dental imager for imaging an intraoral cavity as disclosed herein may include an elongated handle, a head at one end of the elongated handle, a pair of flexible arcuate lateral scanning arms outwardly projecting from the elongated handle, each having a top scanner and a bottom scanner associated therewith for imaging at least a portion of the intraoral cavity, a compass associated with each of the flexible arcuate lateral scanning arms and tracking their angular orientation, a front angled platform associated with the head and carrying a front scanner at an angle between 30 and 60 degrees and a rear angled platform associated with the head and carrying a rear scanner at an angle between 30 and 60 degrees, and a guide having a size and shape for substantial continuous engagement with the intraoral cavity while simultaneously substantially biasing one or more of the scanners at a relatively consistent distance from the intraoral cavity as the dental imager moves relative to the intraoral cavity during imaging.

A communication circuit integral with the elongated handle and in communication with the scanners may selectively transmit imaging data of the intraoral cavity to a computer system or the like for processing, wherein the pair of flexible arcuate lateral scanning arms couple to the head via a flexible coupling. In another aspect of this embodiment, the dental imager may further include an activation sensor that includes an emitter in one of the pair of flexible arcuate lateral scanning arms and a receptor in the other of the pair of flexible arcuate lateral scanning arms. The emitter and the receptor may be generally aligned such that a beam generated by the emitter is receivable by the receptor during non-use and generally blocked by the intraoral cavity during use.

The dental imager may also include a front medial scanning arm and a rear medial scanning arm coupled to the head, wherein the guide may include a lateral roller guide or a lateral pad coupled to each of the pair of flexible arcuate lateral scanning arms at an angle of about 30-45 degrees relative to the lateral scanning arm and the head may be exchangeable with the elongated handle. Additionally, the dental imager may include at least one central scanner mounted to the head having a height relatively less than the roller or the pad and a front medial scanning arm and a rear medial scanning arm coupled to the head. Furthermore, the guide may include a front pad coupled to the front angled platform above the front scanner and a rear pad coupled to the rear angled platform above the rear scanner. In another aspect, the guide may include a roller rotatably coupled to the head and configured to provide rolling support for the dental imager over the intraoral cavity or a pad having a surface permitting sliding movement of the dental imager over the intraoral cavity, and wherein the head pivots relative to the elongated handle by way of a handle bellow or a ball joint.

In another embodiment, a dental imager as disclosed herein includes an elongated handle with a rotatable head coupled to a distal end thereof, the rotatable head having a central platform with a plurality of arcuate scanning arms pivotally coupled thereto by a hinge. The central platform may be rectangular in shape and may permanently connect to the handle. The rotatable head and related central platform connected thereto may be able to rotate 360 degrees relative to the handle. In one embodiment, the central platform may include one or more central scanners designed to scan or image the top of a tooth. The arcuate scanning arms deploy downwardly relative to the handle and are of a shape and size (e.g., arcuate) to at least partially encompass part of a tooth. Each arcuate scanning arm also preferably includes at least one scanner and a roller guide that biases the scanners a desired distance from the surface of the tooth, conducive for imaging thereof, while comfortably rolling along the surface of the tooth or gums as various scans or images of the intraoral cavity are being taken. In one aspect of this embodiment, the dental imager may include a pair of arcuate lateral scanning arms for collecting scanning or imaging data of the sides of the tooth with an upper arm scanner and a lower arm scanner, and an arcuate front and rear scanning arms for collecting scanning or imaging data of the top and back sides of the tooth with medial front and rear scanners. The roller guides generally bias the scanning arms so that the scanners can obtain detailed images of the tooth structure at a relatively consistent distance therefrom. In this respect, such a dental imager may be used in a process to scan and record the contours of an intraoral surface, the data of which may be used to create a digital three-dimensional surface impression printable by a 3D printer or the like.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
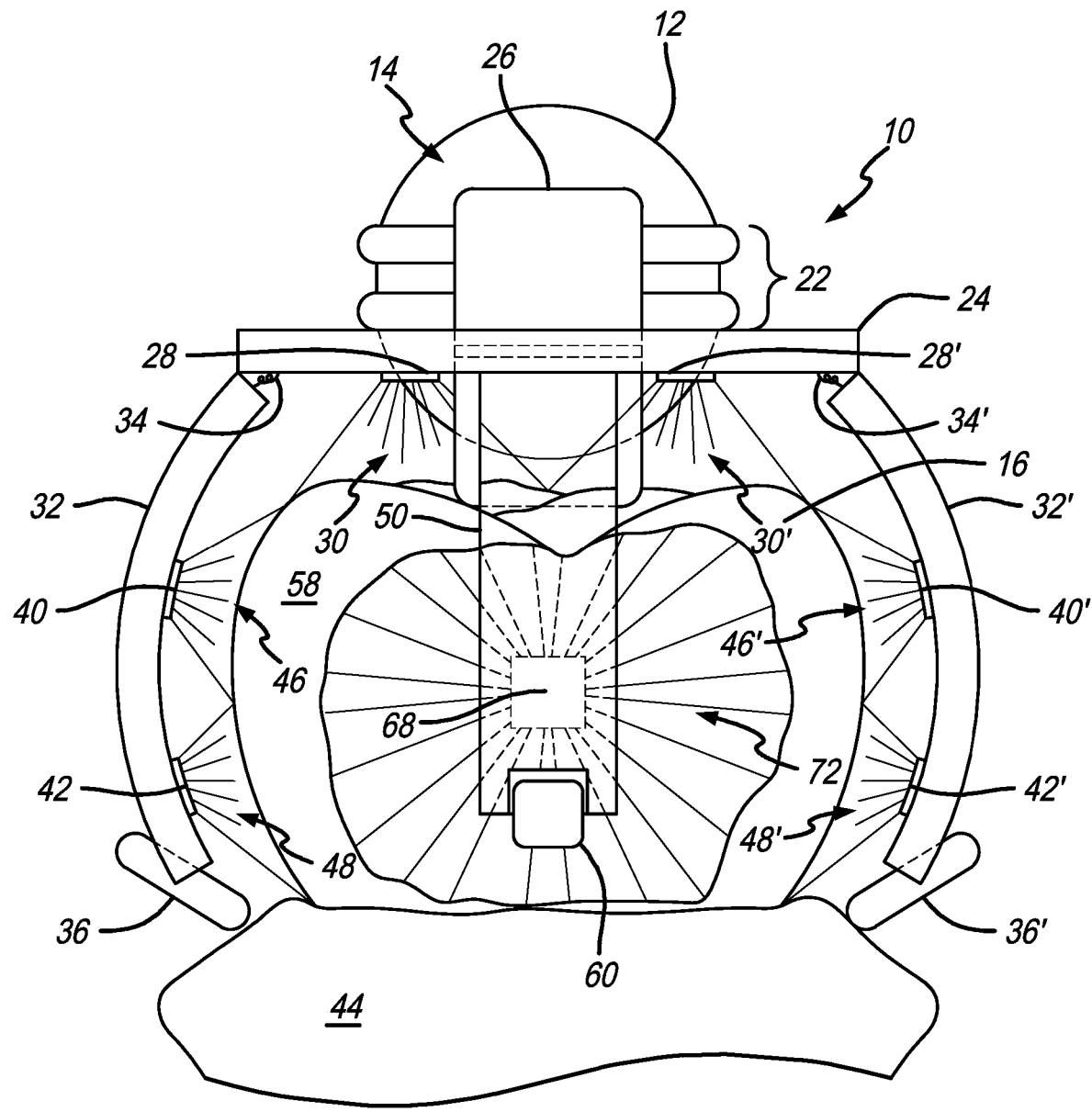
FIG. 1 is a front elevation view of one embodiment of a dental imager as disclosed herein, scanning an intraoral tooth surface.

As shown in the exemplary drawings for purposes of illustration, embodiments for a dental imager as disclosed herein are generally referred to by reference numeral 10 in FIGS. 1-3 and 5-11. In general, the dental imager 10 is a relatively simple design that facilitates quick learning and a "one size fits all" solution, thereby reducing the time to train personnel to take accurate dental impressions, and may be used to image, scan, examine, and/or map the three-dimensional characteristics of intraoral surfaces, such as teeth. For instance, the dental imager 10 can be used to capture the exact shape of a single tooth, multiple teeth in one or more locations, a portion of a dental arc, or the entire dental arc for faster diagnosis. The dental imager 10 also eliminates the inaccuracies of creating dental impressions when a scanned surface is uneven (e.g., teeth surrounded by braces or other dental fixtures) and can provide still images or real-time video output to a viewing monitor. The images or real-time video transmitted by the dental imager 10 may also be magnified, to better evaluate planned mapping sites or perform other dental procedures. When the imaging or scanning is complete, a digital model of the scanned area may then be printed using a 3D printer or the like to create a model mold of the impression. In this respect, the dental imager 10 disclosed herein solves problems related to known procedures that can be cumbersome, uncomfortable, and inaccurate. The dental imager 10 may also significantly reduce, and preferably eliminate, the inaccuracies associated with chemical paste procedures since the chemical paste is no longer needed.

Figure 5:
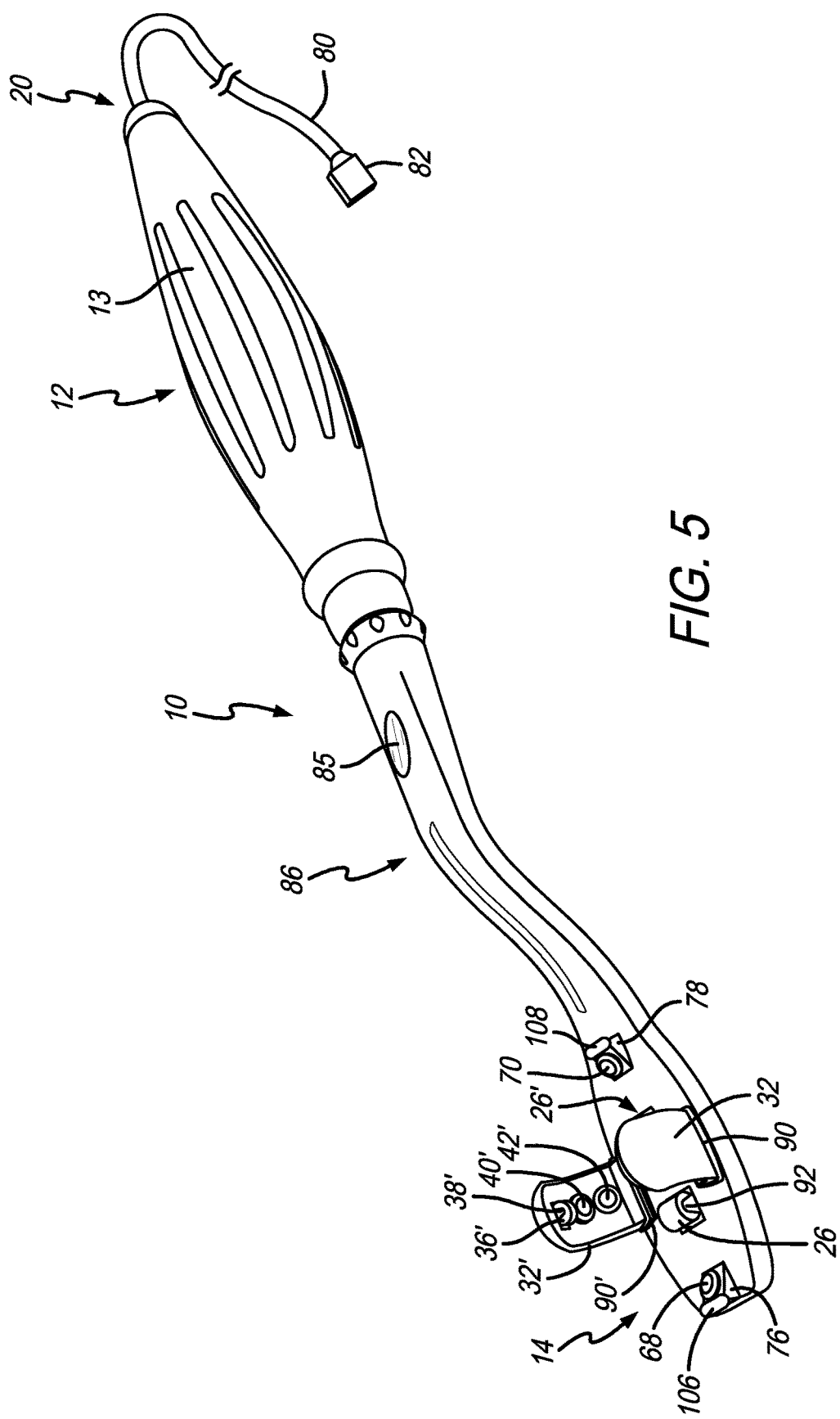
FIG. 5 is a perspective view of another embodiment of the dental imager, including a pair of lateral roller guides integral with the arcuate lateral scanning arms, a pair of central rounded guides, and a stationary front and rear angled scanning platform in a head of the dental imager.

As best shown in FIG. 5, the dental imager 10 may include an elongated handle 12 that may be made from a plastic material and have a structure similar to that of a toothbrush or the like (e.g., approximately 5-6 inches long with a rubber grip and rounded edges). The toothbrush-like elongated handle 12 facilitates select positioning of a distal end 14 thereof along or over one or more of a plurality of teeth 16 within an intraoral cavity 18, as shown schematically in FIG. 3, e.g., while the user may comfortably hold a proximal end 20 (FIGS. 3 and 5) thereof outside of the intraoral cavity 18. In this respect, the elongated handle 12 permits select positioning of the distal end 14 within the intraoral cavity 18 similar to brushing teeth with a toothbrush or the like. This simplifies the process for obtaining a 3D image of certain features of the intraoral cavity 18, such as one or more of the teeth 16.

Figure 2:
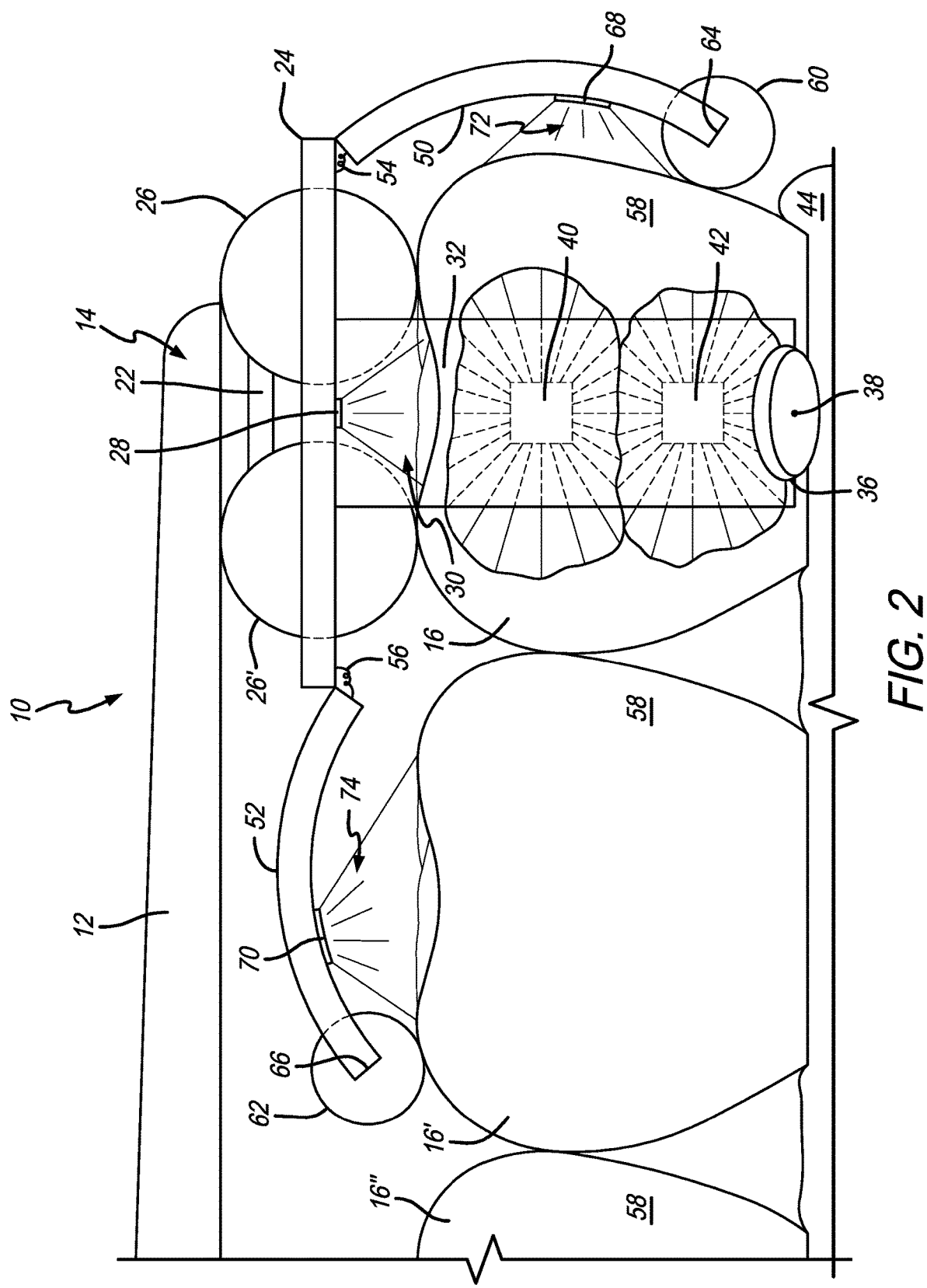
FIG. 2 is a side elevation view of the dental imager of FIG. 1, further illustrating rolling deployment over multiple teeth.

In one embodiment, the dental imager 10 as shown in FIGS. 1-2 may include a rotating head 22 coupled to and projecting downwardly from the distal end 14 (shown best in FIG. 2) by a distance that provides clearance for the length of the elongated handle 12 to be inserted over the teeth 16 in the intraoral cavity 18, for select imaging or scanning therein as disclosed herein. The rotating head 22 is similar to a toothbrush head without bristles, except the rotating head 22 is able to rotate up to 360 degrees relative to the distal end 14 of the elongated handle 12. In this embodiment, a central platform 24 couples to the rotating head 22 in fixed relation relative thereto and incorporates or otherwise supports or connects to at least one central rounded guide 26, and may otherwise support a pair of central rounded guides 26, 26' as illustrated in FIG. 2, to help the central platform 24 track the contours of the teeth 16 when moving the dental imager 10 thereover. In FIG. 2, both of the central rounded guides 26, 26' are surrounded by and attach to the central platform 24. Alternatively, the central platform 24 need not completely surround the central rounded guides 26, 26'. The rotating head 22 and the central platform 24, along with the central rounded guides 26, 26' coupled thereto, may all at least rotate about a longitudinal axis where the rotating head 22 attaches to the distal end 14 of the elongated handle 12. Although, in other embodiments, the rotating head 22 (and the related central platform 24 and the central rounded guides 26, 26') may be able to freely rotate in longitudinal, lateral, and/or vertical axes simultaneously while remaining attached to the distal end 14, such as by way of using a ball joint or the like. The rotating head 22 may be made of a generally rectangular plastic material and may also include an internally disposed electronic compass that tracks the position and angle of the rotatable head 22, to define the correct shape/opening of the dental arc in the digital computer 3D model.

Additionally, the central platform 24 may include at least a pair of central scanners 28, 28' mounted up underneath the central platform 24 in the positions generally shown in FIGS. 1 and 2. In other embodiments, the central scanners 28, 28' may be mounted flush underneath the central platform 24 to provide more clearance. The central platform 24 may be mounted or otherwise formed from the rotating head 22 at approximately a mid-height thereof. Accordingly, in either position, the central scanners 28, 28' are positioned at an approximate predetermined distance above the top of the teeth 16, and are able to capture images, e.g., of the surface area as indicated by a respective set of central beams 30, 30' emitting from the respective central scanners 28, 28' and over the teeth 16, thereby generally indicating the coverage area of the teeth 16 as illustrated in FIGS. 1 and 2.

Moreover, the central platform 24 may further couple to a pair of arcuate lateral scanning arms 32, 32' that extend out from lateral sides of the central platform 24 by way of a respective pair of lateral hinges 34, 34'. In one embodiment, the lateral hinges 34, 34' may be spring-loaded to generally bias the lateral scanning arms 32, 32' toward the interior of the dental imager 10 and otherwise into engagement with the intraoral cavity 18, such as the inside and/or outside surfaces of the teeth 16. The spring-bias mechanism permits the arcuate lateral scanning arms 32, 32' to move in and out about the lateral hinges 34, 34' and to track the shape of the dental arc (e.g., the rounded surface of the teeth 16). In an alternative embodiment, the dental imager 10 may include one or none of the arcuate lateral scanning arms 32, 32'. Here, one or more scanners may be mounted directly to the central platform (e.g., on a protuberance and/or at an angle of 30-60 degrees and/or on an angle of 120-150 degrees) as a replacement for any scanners mounted to the arcuate lateral scanning arms 32, 32', as described in more detail herein. Such embodiments may enhance maneuverability, yet sustain the scanning/imaging scope.

Figure 3:
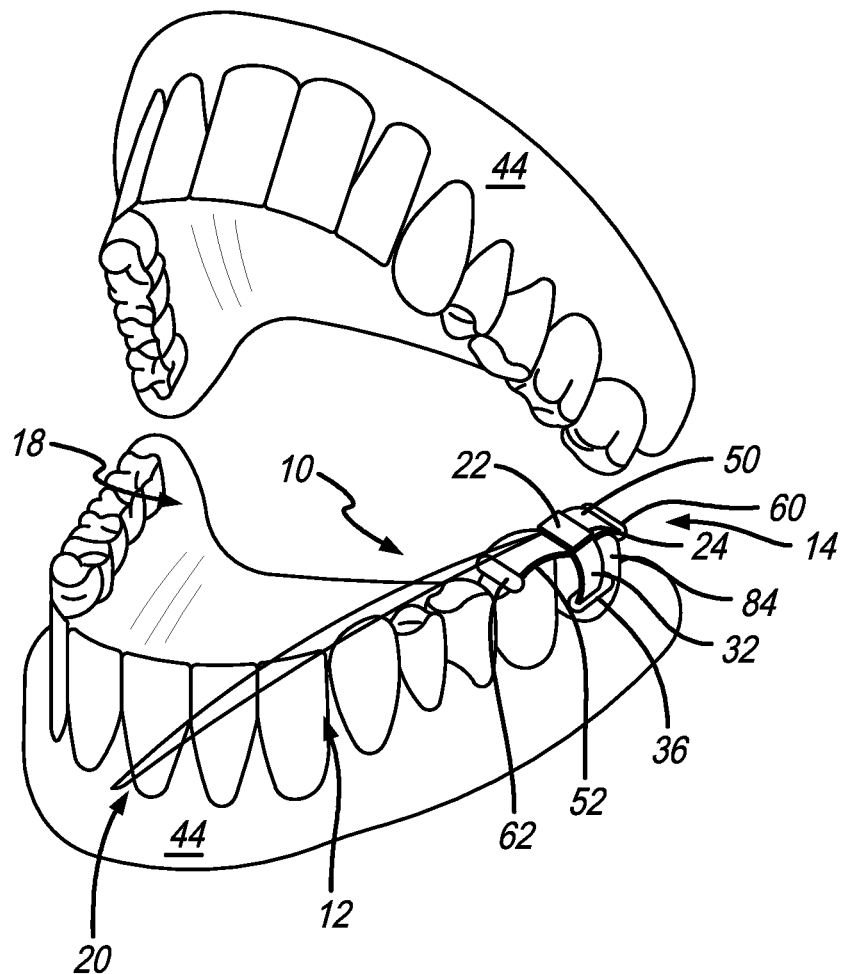
FIG. 3 is an environmental schematic perspective view illustrating the dental imager scanning or imaging a set of human teeth.
Figure 9:
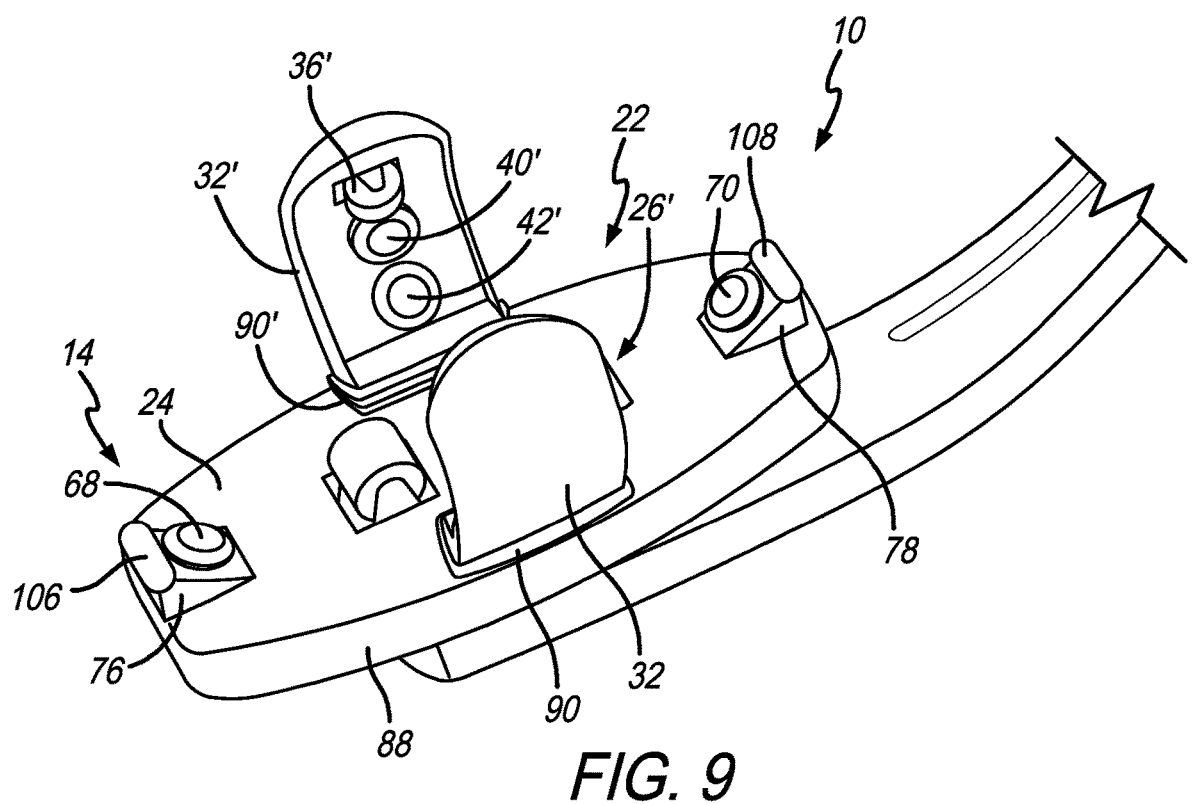
FIG. 9 is a perspective view of another platform-based pivoting head, incorporating the pair of lateral roller guides and the pair of central rounded guides.
Figure 10:
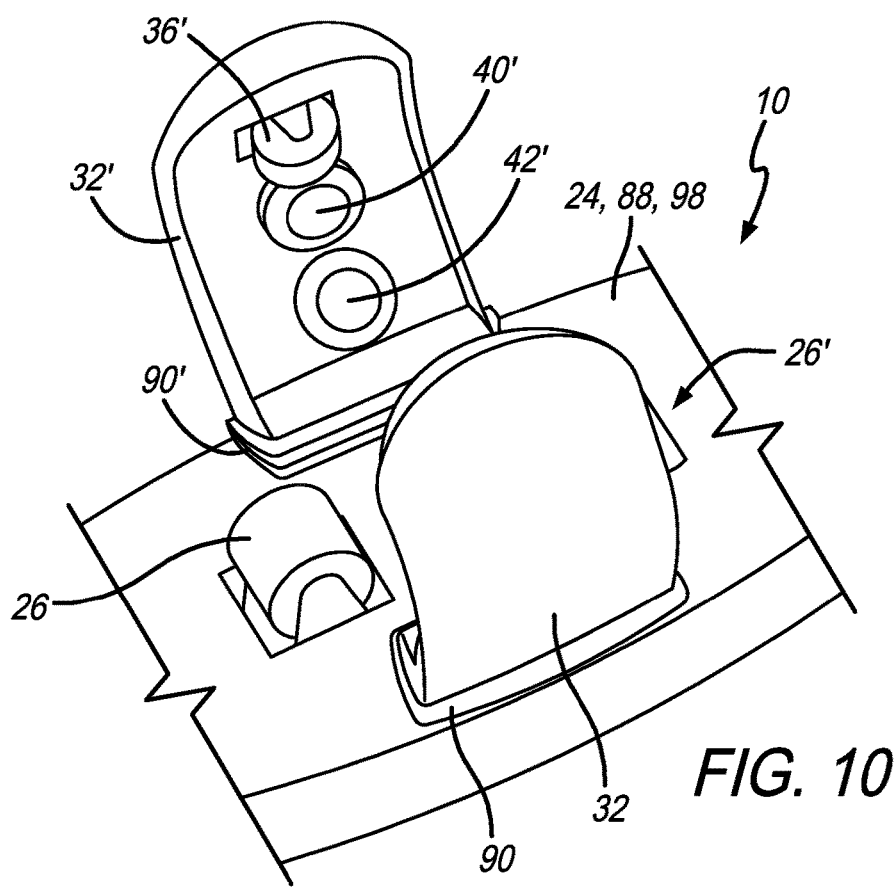
FIG. 10 is an enlarged perspective view of another platform-based pivoting head, similar to FIG. 9

Additionally, each of the arcuate lateral scanning arms 32, 32' may include a respective lateral roller guide 36, 36' rotatably coupled thereto about an axis 38 (FIG. 2) or as integrated into the respective lateral scanning arms 32, 32' as shown in more detail with respect to FIGS. 5 and 9-10. The lateral roller guides 36, 36' may be positioned at an angle (e.g., 30-45 degrees) relative to the arcuate lateral scanning arms 32, 32' to project inwardly from the axis 38 for contact with a portion of the intraoral cavity 18 to prevent the arcuate lateral scanning arms 32, 32' from coming into contact with the teeth 16 or the like. This may be particularly beneficial because the arcuate lateral scanning arms 32, 32' may each include at least one scanner for imaging or scanning the lateral sides of the teeth 16. More specifically, in the embodiment shown with respect to FIG. 1, the arcuate lateral scanning arms 32, 32' each include an upper arm scanner 40, 40' and a lower arm scanner 42, 42'. The inward projection of the lateral roller guides 36, 36' may contact a gum tissue surface 44 and generally bias the arcuate lateral scanning arms 32, 32' away from contacting anything within the intraoral cavity 18. To this end, the arcuate shape of the scanning arms 32, 32' bends away from the shape of the curved teeth 16 to provide clearance along the lateral sides of the teeth 16. This, in turn, biases each of the upper arm scanners 40, 40' and the lower arm scanners 42, 42' away from contacting the teeth 16. Accordingly, each of the upper arm scanners 40, 40' may emit a respective upper beam 46, 46' and each of the lower arm scanners 42, 42' may emit a respective lower beam 48, 48' to capture or record the structure of the lateral sides of the teeth 16. While the embodiment disclosed with respect to FIGS. 1-3 illustrate each arcuate lateral scanning arm 32 having two of the arm scanners 40, 42, alternative embodiments may include fewer scanners (e.g., one), to minimize the number of scanners, or more scanners (e.g., more than two) if more comprehensive coverage is needed and/or desired. The dental imager 10 should be able to image substantially the entire lateral sides of the teeth 16 for purposes of creating as accurate a digital 3D image as possible, although it may be possible to image less than the entire lateral side while still obtaining a usable digital 3D image. In one embodiment, to better maximize coverage, the upper arm scanners 40, 40' and the lower arm scanners 42, 42' may have respective overlapping upper beams 46, 46' and lower beams 48, 48' to better ensure comprehensive coverage. To this end, computer software may be configured to automatically edit out or integrate the overlap based on scanning location calibration and to enhance accurate reproduction of the teeth 16 in a digital 3D environment.

As shown in FIG. 2, the central platform 24 may further include an arcuate front scanning arm 50 and an arcuate rear scanning arm 52 similarly coupled to the central platform 24 by a respective front hinge 54 and a respective rear hinge 56. In this embodiment, the dental imager 10 may include up to four of the scanning arms 32, 32', 50, 52. In this respect, each of the embodiments as disclosed herein may include as few as one lateral scanning arm and as many as four or more of the lateral scanning arms. Similar to the above, the front and rear hinges 54, 56 may be spring-biased to generally bias the respective arcuate front and rear scanning arms 50, 52 toward the interior of the dental imager 10 and otherwise into engagement with an outer surface 58 of the teeth 16. The spring-bias mechanism permits the arcuate front and rear scanning arms 50, 52 to move in and out about the front and rear hinges 54, 56 and to track the shape of the dental arc, such as the curvature of the teeth 16. Each of the hinges 34, 54, 56 may be a one-piece design (e.g., a compression or extension spring), a multi-piece design, free-moving, spring-loaded, or formed of a resilient elastic material. Moreover, while the hinges 34, 54, 56 are disclosed herein as pivotable about a single axis, in alternative embodiments, the hinges 34, 54, 56 may provide for multi-axial pivoting or rotational movement (e.g., a ball joint) along the x-axis, y-axis, and/or z-axis.

In FIG. 2, the arcuate front scanning arm 50 is shown in a lowered position around the back of tooth 16, while the arcuate rear scanning arm 52 is shown in a raised configuration rolling over tooth 16'. The arcuate front and rear scanning arms 50, 52 may also each include a respective medial front roller guide 60 and a medial rear roller guide 62 rotatably coupled thereto about a respective axis 64, 66. The medial front and rear roller guides 60, 62 are of a diameter that allows each to project inwardly from each respective axis 64, 66 for contact with a portion of the intraoral cavity 18, such as the tooth surface 58. This prevents the arcuate front and rear scanning arms 50, 52 from contacting the teeth 16. This may be beneficial in embodiments where the arcuate front and rear scanning arms 50, 52 each include at least one of a respective medial front scanner 68 and a medial rear scanner 70. The arcuate shape of the scanning arms 50, 52 may similarly follow the contour of the curved teeth 16 (thereby bending away therefrom), to provide clearance along the medial and top sides of the teeth 16 as shown. This, in turn, biases each of the medial front and rear scanners 68, 70 away from contacting the teeth 16. Accordingly, each of the medial front and rear sensors 68, 70 may emit a respective front beam 72 and a rear beam 74 to capture or record the structure of the medial and upper sides of the teeth 16 (in place of or to compliment the central scanners 28, 28'). In alternative embodiments, the dental imager 10 may include one or none of the arcuate front scanning arm 50 and/or the arcuate rear scanning arm 52. Alternatively, one or more scanners may be mounted directly to the central platform 24 on an angled stationary front platform 76 and/or on an angled stationary rear platform 78, as shown with respect to FIGS. 8 and 9. Here, the angle of the platforms 76, 78 may be 30-60 degrees and/or 120-150 degrees and support the respective medial front and rear scanners 68, 70 as a replacement for scanners mounted to the arcuate front scanning arm 50 and/or the arcuate rear scanning arm 52. The embodiments shown with respect to FIGS. 8 and 9 may enhance maneuverability, yet sustain the scope of scanning/imaging.

Moreover, each of the arcuate front scanning arm 50 and/or the arcuate rear scanning arm 52 may also include more or less of the respective medial front and rear scanners 68, 70, as needed and/or desired. Although, the dental imager 10 should include enough scanners to substantially image the entire medial surface area of the teeth 16 for purposes of creating as accurate a digital 3D image as possible. For example, to enhance coverage, the front beam 72 and/or the rear beam 74 may overlap with the central beams 30, 30' emitted by one or more of the central scanners 28, 28' to ensure comprehensive coverage. Although, overlapping coverage may not be needed to create an accurate 3D image. To this end, computer software may be configured to automatically edit out gaps or unneeded overlap based on calibration among the scanners 28, 68, 70 and to enhance accurate digital 3D reproduction of the teeth 16.

The central scanners 28, 28', the upper arm scanners 40, 40', the lower arm scanners 42, 42', and/or the medial front and rear scanners 68, 70 may couple to a power source that provides activation energy thereto. For example, in one embodiment, the proximal end 20 may include a non-removable or plug-in cord 80 that transfers power to the dental imager 10 on-demand. In this embodiment, the cord may include a USB connector 82 wherein the dental imager 10 can also transfer data to a computer system, when connected thereto. Alternatively, the cord could be a fiber optic cord used to transfer information. In another embodiment, the dental imager 10 may include a removable or non-removable rechargeable battery within the handle 12. In this embodiment, the dental imager 10 may be rechargeable by placing the proximal end 20 into a charger holder, and charged with technology used with modern electric toothbrushes. In another embodiment, the handle 12 may house a removable battery (e.g., a AAA battery) that can be selectively removed and replaced as needed.

The corresponding computing device may receive, store, analyze, and reconstruct the data obtained by one or more of the scanners 28, 40, 42, 68, 70 into a cohesive digital three-dimensional impression. As shown in FIG. 1 and mentioned above, the central scanners 28, 28', the upper arm scanners 40, 40', the lower arm scanners 42, 42', and/or the medial front and rear scanners 68, 70 may blanket or substantially blanket the scanned tooth surface 58 with the aforementioned central beams 30, 30', the upper and lower beams 46, 48, and the front and rear beams 72, 74. In this configuration, the scanners 28, 40, 42, 68, 70 have a higher chance of capturing all indentations, cracks, and spaces in the teeth 16, especially when positioned at an angle relative to the tooth surface 58. In this respect, the positioned angle may vary from scanner-to-scanner along the respective arcuate scanning arms 32, 50, 52. The beams 30, 46, 48, 72, 74 may correspond to visible light that can be recorded and processed by a computer software system. Projection and recordation of such visible light may allow for three-dimensional mapping via optical triangulation. Alternatively, the central scanners 28, 28', the upper arm scanners 40, 40', the lower arm scanners 42, 42', and/or the medial front and rear scanners 68, 70 may be formed as non-contact passive scanners that emit no light. In this embodiment, the scanners 28, 40, 42, 68, 70 may rely on detected reflected light from the scanned tooth surface 58 in conjunction with stereoscopic or photometric sensors to recreate a three-dimensional digital representation. In another embodiment, the scanners 28, 40, 42, 68, 70 may use active or passive optical or electro-optical scanning technology to measure and record the surface under examination. The scanners 28, 40, 42, 68, 70 may also electronically measure and record the contours of the scanned tooth surface 58 through use of electronic imaging sensors, such as CCD or CMOS imaging sensors. In another embodiment, the scanners 28, 40, 42, 68, 70 may be cameras that take pictures of or otherwise record the surface structure of the teeth 16. In this embodiment, the computer software could convert pictures/recordings taken at different positions along the dental arc into a digital 3D model.

Figure 4:
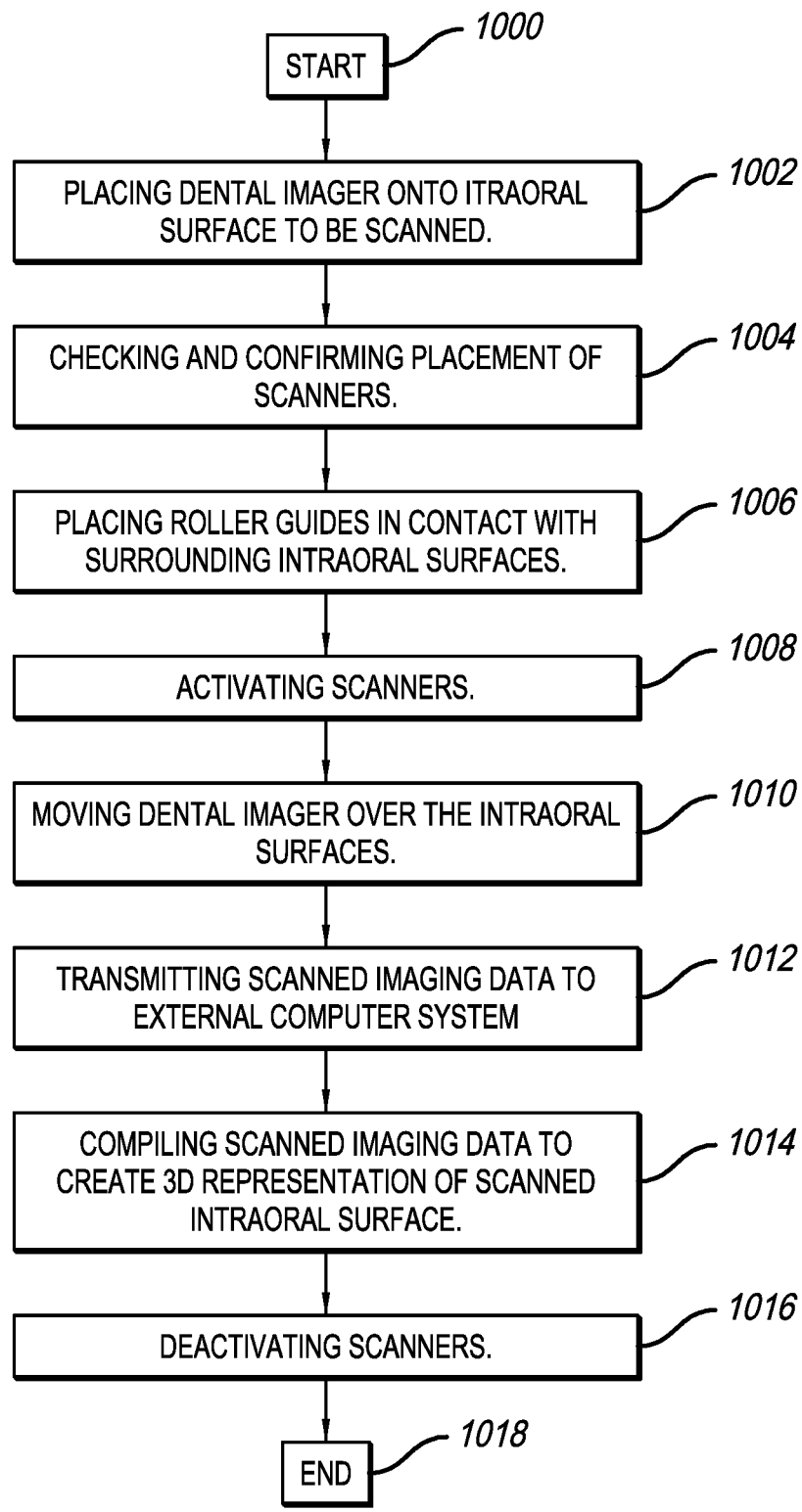
FIG. 4 is a flow-chart illustrating a process for scanning or imaging an intraoral surface using the dental imagers as disclosed herein.

FIG. 3 is an environmental perspective view of one embodiment of the dental imager 10 deployed in the intraoral cavity 18 and FIG. 4 illustrates a related process (1000) for scanning the intraoral cavity 18 using the dental imager 10. For instance, the scanning or imaging process (1000) starts by placing the dental imager 10 onto the intraoral surface 18 to be scanned (1002). As shown in FIG. 3, one would hold the proximal end 20 of the dental imager 10 and extend the distal end 14 into the intraoral cavity 18 for placement of the rotating head 22 over a mandibular third left molar 84. Of course, this is only one example of many locations within the intraoral cavity 18 where the user could start. As such, the starting location should not be limited only to the mandibular third left molar 84. The next step (1004) is to check and confirm that the arcuate lateral scanning arms 32, 32' and the arcuate front and rear scanning arms 50, 52 are free to pivot throughout their respective rotational arcs. The next step (1006) is to ensure that the central rounded guides 26, 26', the lateral roller guides 36, 36', and/or the medial front and rear roller guides 60, 62 contact the area surrounding the intraoral surface to be scanned (e.g., the gum surface 44 or the surface 58 of the teeth 16, such as the mandibular third left molar 84 in FIG. 3). Once in place, the next step (1008) is to activate the central scanners 28, 28', the upper arm scanners 40, 40', the lower arm scanners 42, 42', and/or the medial front and rear scanners 68, 70.

In the event the scanners 28, 40, 42, 68, 70 are not already operating, the user may have the option of pushing a switch 85 (FIG. 5) to turn the dental imager 10 to an "on" position to begin scanning or taking readings. The same switch 85 may be used to turn the dental imager 10 to an "off" position to deactivate scanning. In one embodiment as shown in FIG. 5, the switch 85 may be in the shape of a ring (i.e., similar to the size and shape of a finger). Depressing the switch 85 may activate image/shape capturing and releasing the switch 85, so that it is no longer depressed, may deactivate said image/shape capturing. Of course, the switch 85 could also be a button or the like designed to activate and/or deactivate the dental imager 10 on-demand.

Alternatively, the dental imager 10 may further include a sensor to determine when the dental imager 10 is in place and ready for activation and scanning. In this respect, the dental imager 10 may automatically and/or semi-automatically sense when to activate and/or deactivate. In one embodiment, the dental imager 10 may include a sensor to activate and/or deactivate scanning by sensing when an object (e.g., one or more of the teeth 16) is positioned in between the arcuate lateral scanning arms 32, 32'. In one embodiment, one of the arcuate lateral scanning arms 32 may include an emitter (e.g., capable of emitting an infrared beam or the like) and the other arcuate lateral scanning arm 32' may include a receptor (e.g., capable of detecting reception of the emitted infrared beam or the like). During non-use, the emitter may be able to transmit the beam to the receptor, for detection by the receptor. In this state, the dental imager 10 may be able to determine that no object is placed between the arcuate lateral scanning arms 32, 32' such that the dental imager 10 should remain deactivated. Then, when the user places the dental imager 10 into the intraoral cavity 18 and over, e.g., one or more of the teeth 16 (FIG. 3), transmission of the beam from the emitter to the receptor is interrupted. Here, the dental imager 10 can identify a state wherein one or more of the teeth 16 are blocking transmission of the beam from the emitter to the receptor such that the dental imager 10 should activate and start scanning. The dental imager 10 may then again deactivate once the dental imager 10 is removed from the intraoral cavity 18 and transmission of the beam from the emitter to the receptor resumes. When the dental imager 10 is activated as disclosed herein, such activation may also activate a positional tracker inside the head and/or the arcuate lateral scanning arms 32, 32'.

To start, as shown in FIG. 3, and more specifically with respect to FIG. 2, the arcuate front scanning arm 50 may overhang the back of the mandibular third left molar 84 to scan or image the rear side thereof, while the arcuate lateral scanning arms 32, 32' are in the positions generally shown in FIG. 2 to scan or image the lateral sides of the teeth 16. Here, the arcuate rear scanning arm 52 is generally raised and in a position to scan the top of the tooth 16'. The next step (1010) is to scan the desired area. For example, the user may pull the elongated handle 12 away from the mandibular third left molar 84 along the top of the dental arc so that the central rounded guides 26, 26' gently travel across the top of the teeth (e.g., the teeth 16-16'' in FIG. 2). In this respect, the medial rear roller guide 62 permits rearward or retracting rolling movement of the dental imager 10 along the dental arc by way of rotational movement about the rear axis 66. At the same time, the arcuate lateral scanning arms 32, 32' move relative to the teeth 16 by way of rolling engagement of the lateral roller guides 36, 36' about the respective axes 38, 38'. Additionally, moving the dental imager 10 from right-to-left (FIG. 2) causes the arcuate front scanning arm 50 to be pulled up from behind the back part of the mandibular third left molar 84. In this respect, the arcuate front scanning arm 50 pivots relative to the central platform 24 about the front hinge 54, which permits the arcuate front scanning arm 50 to move from a general vertical position shown in FIG. 2 to a general horizontal position (e.g., as shown in FIG. 2 with respect to the arcuate rear scanning arm 52). Thus, a user is able to scan one or more of the teeth 16 through deployment of the dental imager 10 over the desired tooth (or teeth) at one or more locations within the intraoral cavity 18.

The next step (1012) is to transmit the scanned image data from the dental imager 10 to an external computer system. The data could include a scan of a single tooth, multiple teeth, a portion of the dental arc, or an entire dental arc. Step (1012) could be completed after the scanning step (1010), or it could be completed simultaneously, such as in real-time. For example, information collected by the scanners 28, 40, 42, 68, 70 may be transmitted to an external computer via a hardwire connection such as a USB connector 82 or a fiber optic connection. Alternatively, the dental imager 10 may transmit data wirelessly (e.g., by way of an infrared transmitter, Wi-Fi transmitter, Bluetooth, etc.). In the case of wireless transmission, the handle may include a battery that provides power for the operation of the scanners 28, 40, 42, 68, 70 and the wireless transmitter. For hardwire connections (e.g., the USB connector 82 and/or a fiber optic connector), power may be supplied directly to the dental imager 10 by way of the cord 80 connected to a computer or other power source. The elongated handle 12 of the dental imager 10 may also incorporate one or more buttons or the like (e.g., the switch 85) that activate one or more of the scanners 28, 40, 42, 68, 70 and/or initiates transmission of scanning data, such as with one touch operation. Thereafter, the next step (1014) involves the computer system software analyzing the scanned image data to create a detailed three-dimensional representation of the scanned tooth surface area. The user then deactivates the scanners 28, 40, 42, 68, 70 as part of step (1016) and the process ends as part of step (1018).

FIGS. 5-11 illustrate alternative embodiments of the dental imager 10 as disclosed herein. For instance, in FIG. 5, the dental imager 10 is shown having the distal end 20 with the plug-in cord 80 extending therefrom and having the USB connector 82 for coupling to a computer or the like. Although, as mentioned above, the plug-in cord 80 and/or the USB connector 82 could be replaced with other technology, such as a fiber optic connector or a wireless transmitter integrated into the elongated handle 12. The elongated handle 12 includes the rubber grip 13 of generally larger diameter for ease of handling. The elongated handle 12 then transitions into a neck region 86 that generally bends down and away from the section of the elongated handle 12 with the rubber grip 13 such that a static head 88 or the like, as disclosed herein, at the distal end 14 of the dental imager 10 is positioned in a plane generally lower than the section with the rubber grip 13. This may facilitate ease of use as the user can generally hold the dental imager 10 above, e.g., the teeth 16 for placement thereover during scanning. In this embodiment, the static head 88 is, of course, fixed relative to the curvature of the neck region 86 and the rubber grip 13.

In this embodiment, the static head 88 includes the pair of arcuate lateral scanning arms 32, 32' having the pair of lateral roller guides 36, 36' (e.g., at a 30-60 degree angle), the pair of upper scanners 40, 40', and the lower scanners 42, 42', as generally disclosed above. Although, in this embodiment, the lateral roller guides 36, 36' are formed integral with the arcuate lateral scanning arms 32, 32', as opposed to being coupled to or otherwise extending out from the ends thereof, such that the axes 38 are positioned to the inside of and otherwise generally shielded from the exterior by the housing of the respective arcuate lateral scanning arms 32, 32'. Here, again, the lateral roller guides 36, 36' may be positioned generally at an approximate 30-60 degree angle relative to the intraoral cavity 18 and may rotate about their respective axes 38, 38' to further facilitate rolling movement of the dental imager 10 along the teeth 16, thereby biasing the upper scanners 40, 40' and the lower scanners 42, 42' away from the tooth surface 58.

This embodiment also discloses the angled stationary front platform 76 having the medial front scanner 68 thereon and the angled stationary rear platform 76 having the medial rear scanner 70 thereon and being formed as part of the static head 88, as opposed to being formed as part of the central platform 24, as described above. Although, here again, the angled nature of the front and rear platforms 76, 78 with the medial front and rear scanners 68, 70 thereon permits additional viewing and/or scanning of the medial portion of the teeth 16 as the dental imager 10 passes thereover, as disclosed herein.

Additionally, FIG. 5 illustrates that the arcuate lateral scanning arms 32, 32' may couple to the static head 88 about a respective pair of pivotable scanning arm bellows 90, 90'. The pivotable scanning arm bellows 90, 90' may include a flexible accordion-shaped outer rubber bellow, as shown, that encloses a spring hidden therein. The enclosed spring gives the arcuate lateral scanning arms 32, 32' the flexibility to adapt to the shape of the dental arc while the dental imager 10 moves along the dental arc during scanning. Although, while the embodiments disclosed herein illustrate the pivotable scanning arm bellows 90, 90' including the flexible accordion-shaped outer rubber bellow, possibly for hygienic reasons, other embodiments may include a similar spring mechanism that is not necessarily enclosed by the accordion-shaped outer rubber bellow. Here, the spring of the pivotable scanning arm bellows 90, 90' would be exposed and may facilitate easier long-term maintenance. In another alternative embodiment, the pivotable scanning arm bellows 90, 90' may be sufficiently rigid, yet flexible, to permit biased movement without the use of a spring.

FIG. 5 also discloses an alternative embodiment wherein the central rounded guides 26, 26' are formed integral with the static head 88, as opposed to the central platform 24, as disclosed in other embodiments herein. Here, the central rounded guides 26, 26' rotate about an axis 92 (the axis 92' being hidden in FIG. 5) to facilitate rolling movement of the dental imager 10 over the top of the teeth 16 during scanning.

Figure 6:
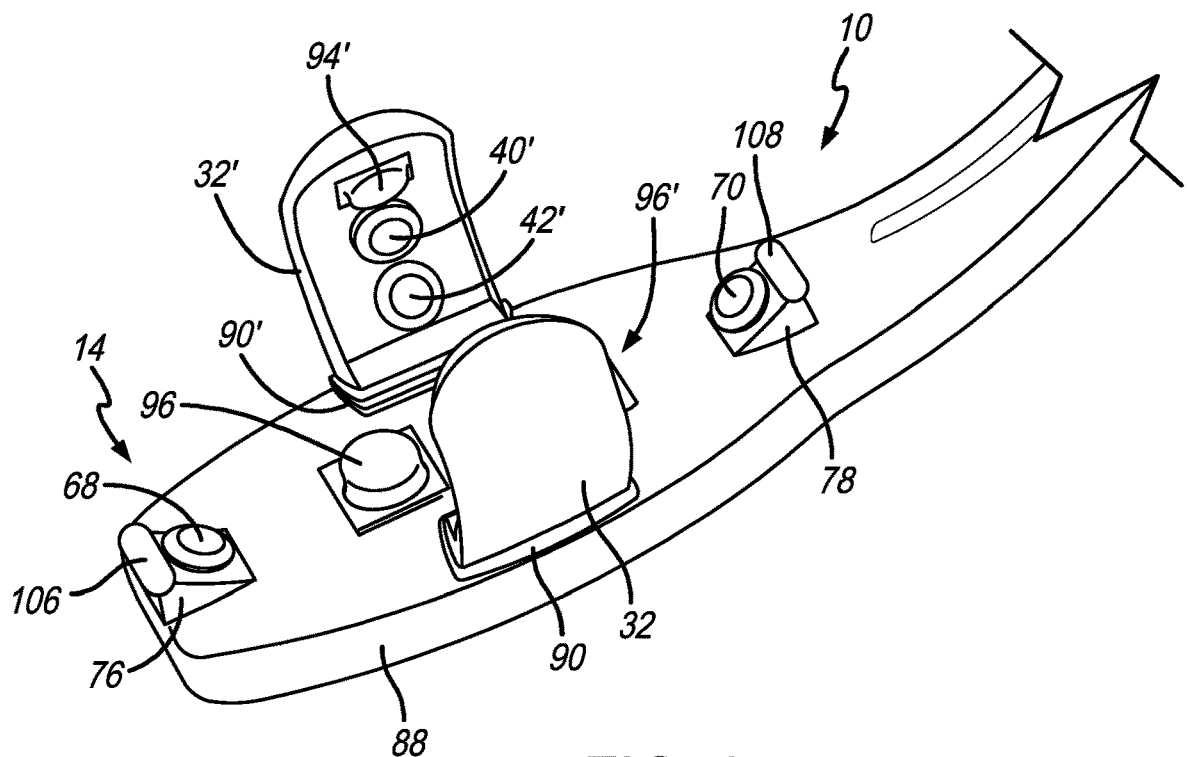
FIG. 6 is a perspective view of an alternative head for the dental imager, including a pair of lateral pads integral with the arcuate lateral scanning arms in place of the pair of lateral roller guides and a pair of central pads in place of the central rounded guides.

FIG. 6 illustrates an alternative embodiment of the static head 88 similar to FIG. 5 with respect to the arcuate lateral scanning arms 32, 32' coupled to the static head 88 by way of the scanning arm bellows 90, 90' and having the upper arm scanners 40, 40' and the lower arm scanners 42, 42' thereon, along with the medial front scanner 68 on the angled stationary front platform 76 and the medial rear scanner 70 on the angled stationary rear platform 78. Although, in FIG. 6, the lateral roller guides 36, 36' have been replaced with a pair of lateral pads 94, 94' and the central rounded guides 26, 26' have been replaced with a pair of respective central pads 96, 96'. Any of the pads 94, 96 may be made from a Teflon material or the like to facilitate sliding movement of the pads 96, 96 over the teeth 16 during scanning, similar to the guides 26, 36.

Figure 7:
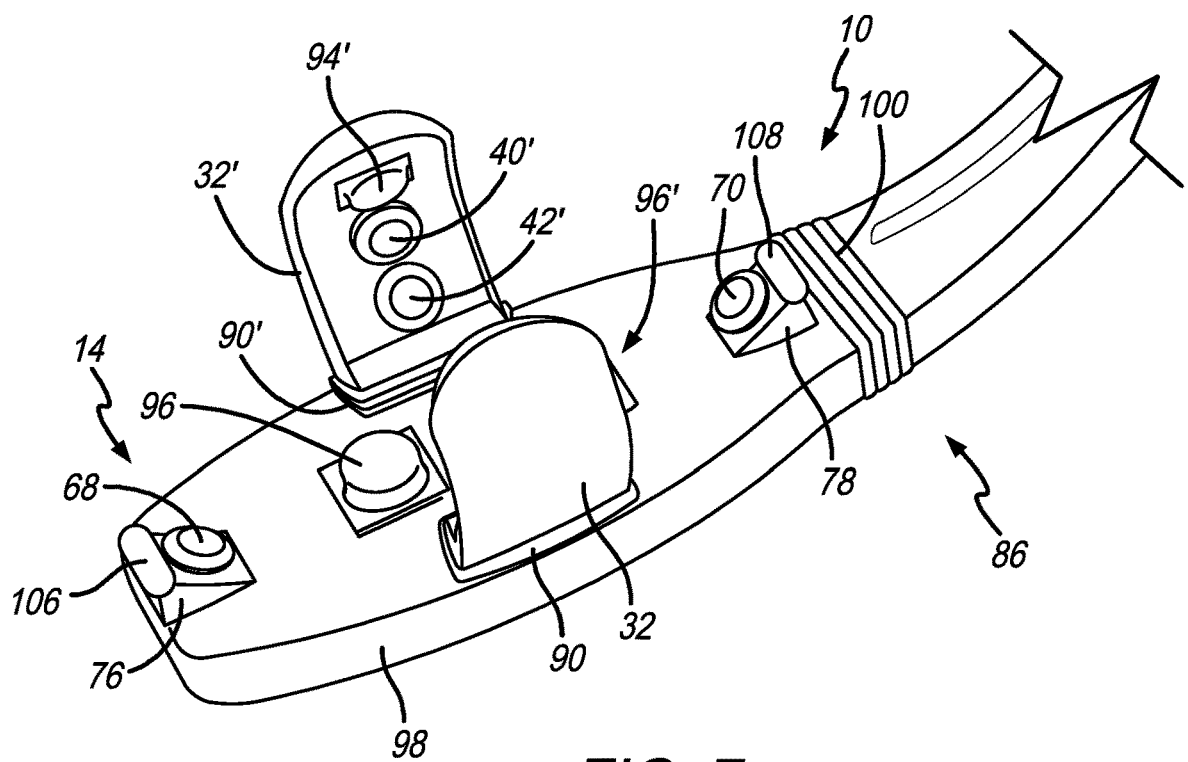
FIG. 7 is a perspective view of a dental imager having a handle bellow permitting movement of the head relative to the elongated handle.

FIG. 7 illustrates an alternative embodiment wherein the dental imager 10 includes a pivotable head 98 as opposed to the rotating head 22 or the static head 88, as disclosed above. Here, the pivotable head 98 couples to the neck region 86 by a handle bellow 100 having a flexible accordion-shaped outer rubber bellow, similar to that described above with respect to the scanning arm bellows 90, 90'. Likewise, the flexible accordion-shaped outer rubber handle bellow 100 may enclose a spring hidden therein that otherwise allows the pivotable head 98 to move or pivot relative to the neck region 86 by up to 180 degrees up and/or down. In an alternative embodiment, the accordion-shaped outer rubber bellow may enclose a ball joint, wherein the pivotable head 98 may move up to 180 degrees up/down and/or left/right relative to the neck region 86. The pivoting nature of the head 98 provides added flexibility to adapt the dental imager 10 to the shape of the dental arc while the dental imager 10 moves along the dental arc during scanning. Although, while the embodiments disclosed herein illustrate the handle bellow 100 including the flexible accordion-shaped outer rubber bellow, possibly for hygienic reasons, other embodiments may include a similar spring or ball joint mechanism that is not necessarily enclosed by the accordion-shaped outer rubber bellow. Here, the spring or ball joint mechanism of the handle bellow 100 may be exposed and may facilitate easier long-term maintenance. In another alternative embodiment, the handle bellow 100 may be sufficiently rigid, yet flexible, to permit biased movement without the use of a spring or ball joint.

Although, in general, the arcuate lateral scanning arms 32, 32' may be movable relative to the respective central platform 24, the static head 88, and/or the pivotable head 98, depending on the embodiment. This can be accomplished by way of a spring-based design (e.g., as shown best in FIGS. 1-2), by forming at least a portion (e.g., the bottom or near where flexing occurs) of the arcuate lateral scanning arms 32, 32' from a flexible material (e.g., rubber), by forming the entire arcuate lateral scanning arms 32, 32' from a flexible material such as rubber, or by way of the scanning arm bellows 90, 90' (e.g., as shown with respect to FIGS. 5-10) with or without a spring, ball joint, or other type of mechanical biasing device therein. In the embodiment without a spring, the elasticity and flexibility of the bellow may provide sufficient movement needed to track the dental imager 10 along the anatomy of the dental arc of the patient. To this end, any of the versions of the dental imager 10 as disclosed herein having flexible or movable arcuate lateral scanning arms 32, 32' and/or arcuate front and/or rear scanning arms 50, 52 may also have a position sensor (e.g., angle) inserted therein, to perceive the angle at which each arm 32, 50, 52 is being flexed.

The pivotable head 98 illustrated in FIG. 7 is otherwise substantially similar to the static head 88 shown and described with respect to FIG. 6, including the arcuate lateral scanning arms 32, 32' coupled to the pivotable head 98 by way of the scanning arm bellows 90, 90' and having the upper arm scanners 40, 40' and the lower arm scanners 42, 42' thereon, the medial front scanner 68 on the angled stationary front platform 76, the medial rear scanner 70 on the angled stationary rear platform 78, the lateral pads 94, 94' and the central pads 96, 96'. Although, it may be possible to interchange one or more of the features as disclosed herein, such that, e.g., the pivotable head 98 could be used with the lateral roller guides 36, 36' in place of the lateral pads 94, 94' and/or the pivotable head 98 could be used with the central rounded guides 26, 26' in place of the central pads 96, 96'.

Figure 8:
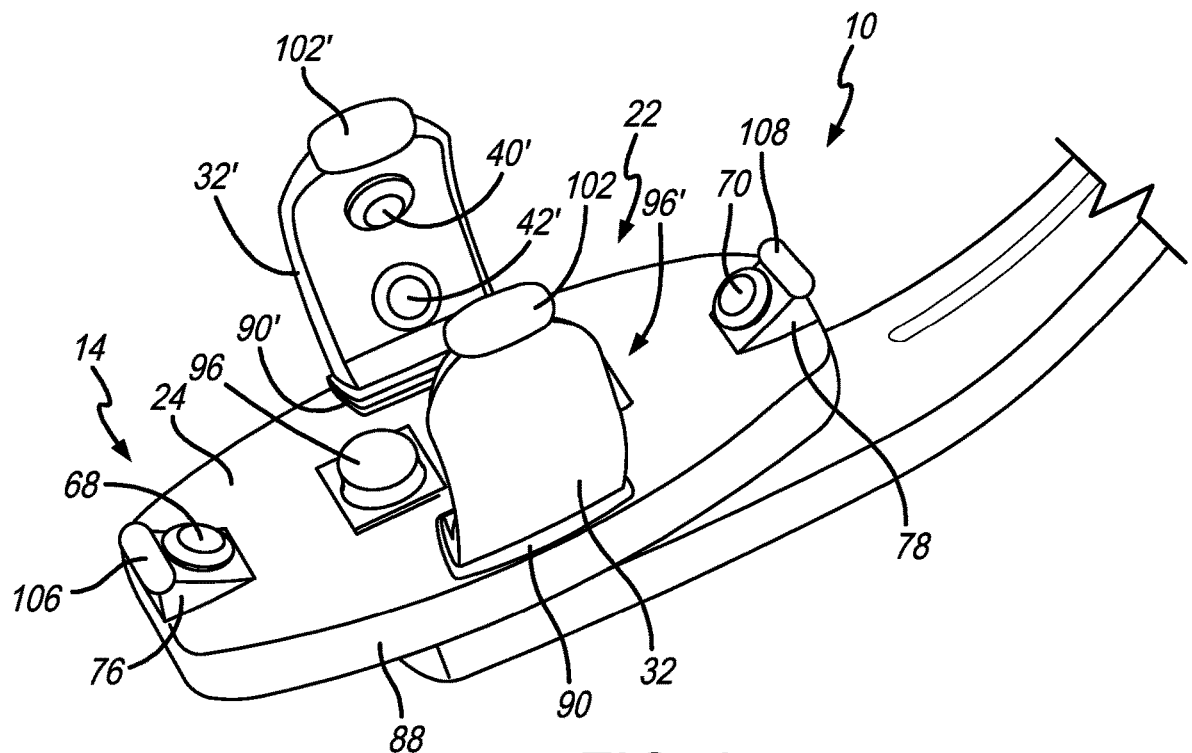
FIG. 8 is a perspective view of another embodiment of a platform-based rotatable head for use with the dental imagers disclosed herein, including a pair of end pads at ends of the arcuate lateral scanning arms.

FIGS. 8 and 9 illustrate alternative embodiments of the dental imager 10 with respect to the central platform 24, similar to the embodiments described above with respect to FIGS. 1-3. FIG. 8 illustrates that the central platform 24 of the rotatable head 22 may include the arcuate lateral scanning arms 32, 32' coupled to the central platform 24 by way of the scanning arm bellows 90, 90' and having the upper arm scanners 40, 40' and the lower arm scanners 42, 42' thereon, the medial front scanner 68 on the angled stationary front platform 76, the medial rear scanner 70 on the angled stationary rear platform 78, the lateral pads 94, 94' and the central pads 96, 96'. Although, it may be possible to interchange one or more of the features as disclosed herein, such that, e.g., the rotating head 22 could be used with the lateral roller guides 36, 36' in place of the lateral pads 94, 94' and/or the rotating head 22 could be used with the central rounded guides 26, 26' in place of the central pads 96, 96'. To this end, FIG. 8 further illustrates that the arcuate lateral scanning arms 32, 32' may include a respective set of end pads 102, 102' made from Teflon or the like for guiding movement of the dental imager 10 during use. Additionally, FIG. 9 may include the central rounded guides 26, 26' (as opposed to the central pads 96, 96' shown in FIG. 8) and the lateral roller guides 36, 36' (as opposed to the lateral pads 94, 94' shown in FIG. 8).

FIG. 10 is an enlarged perspective view of the scanning arm bellows 90, 90' coupling the arcuate lateral scanning arms 32, 32' to any of the central platform 24, the static head 88, and/or the pivotable head 98.

Figure 11:
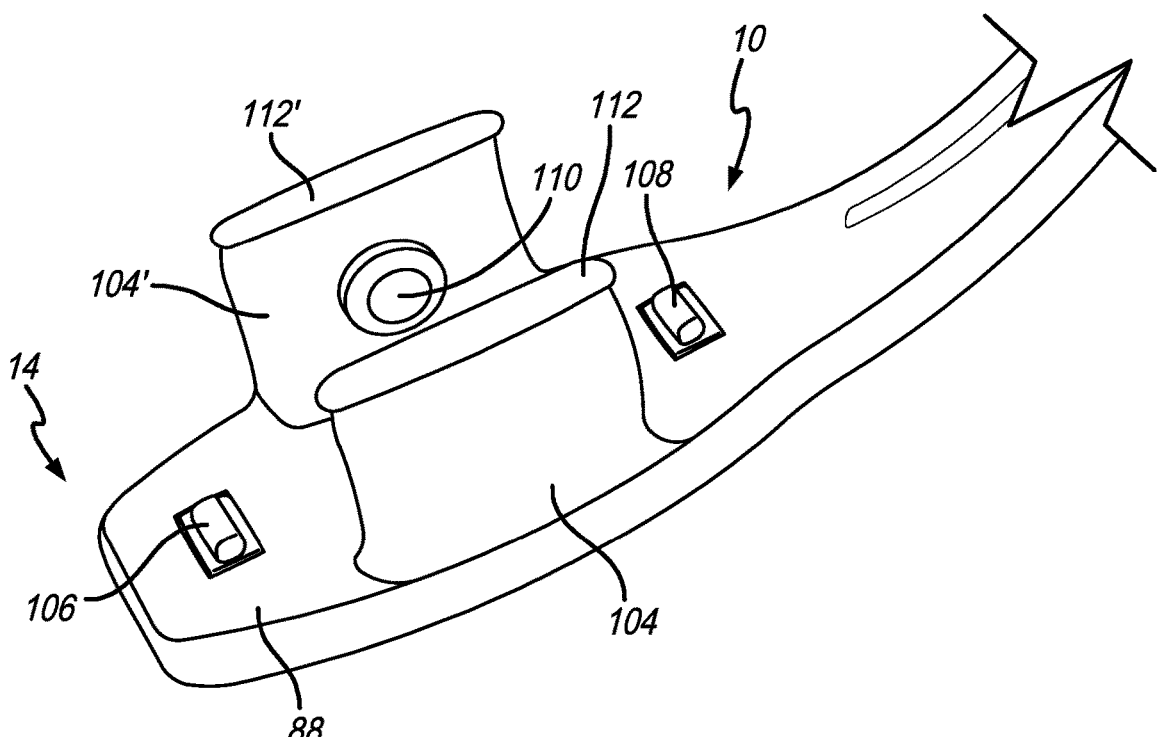
FIG. 11 is a perspective view of another embodiment of the dental imager, illustrating a pair of static arcuate lateral scanning arms along with a front pad and a rear pad.

Lastly, in another alternative embodiment, FIG. 11 illustrates wherein the dental imager 10 may include a pair of static arcuate lateral scanning arms 104, 104' immovable relative to the static head 88. In this respect, one or both of the static arcuate lateral scanning arms 104, 104' may be in fixed relation relative to the to the static head 88, or may be in fixed relation relative to the central platform 24 or pivotable head 98 when used in connection with other embodiments disclosed herein. Moreover, FIG. 11 illustrates that the static arcuate lateral scanning arms 104, 104' may include a single standalone scanner 110, 110' such that the dental imager 10 in FIG. 11 includes two of the standalone scanners, 110, 110', one in each of the static arcuate lateral scanning arms 104, 104'. Here, the static arcuate lateral scanning arms 104, 104' may function to detach the tongue and cheeks from the teeth 16, so the standalone scanners 110, 110' are able to better capture a clean image of the intraoral cavity 18. Additionally, the upper edges of the static arcuate lateral scanning arms 104, 104' may include a respective set of elongated pads 112, 112' to enhance comfort and guidance when scanning within the intraoral cavity 18. Here, like the other pads 94, 96, 102, 106, 108, the elongated pads 112, 112' may be made from a Teflon material or the like. While FIG. 11 illustrates an embodiment wherein the dental imagers 10 includes the static head 88, the static arcuate lateral scanning arms 104, 104' and the related standalone scanners 110, 110' may also be compatible for use with the rotating head 22 (and associated central platform 24) or the pivotable head 98. As such, the dental imager 10 with the static arcuate lateral scanning arms 104, 104' and the related standalone scanners 110, 110' may be simpler and require less computational power since the standalone scanners 110, 110' do not move relative to the static head 88. Thus, the post processing software may not need to determine the position of the standalone scanners 110, 110' relative to each other or relative to the static head 88.

In an example where the dental imager 10 includes only one of the lateral scanning arms 32, 32' or one of the static arcuate lateral scanning arms 104, 104', the user may need to first pass the select arcuate lateral scanning arm 32 or 104 along the inside of the dental arc, then conduct a second pass along the outside of the dental arc (or vice-versa) to obtain a complete scan.

In general, various technologies known in the art may be used to create the digital computer 3D model of the dental arc, including, but not limited to, time of flight (ToF), stereoscopic vision, light field moment imaging, fixed structured light, programmable structured light (DLP), and/or 3D and/or 4D ultrasound (sonography). Additionally, one or more of the scanners 28, 40, 42, 68, 70, 110 may use image/shaping capture technologies known in the art, such as, but not limited to, laser technology, digital camera technology, ultrasound sensor technology, and/or light emitting diode (LED) technology.

More specifically, structured light 3D imaging may require the integration of at least one projector and at least one camera per scanner (e.g., in one or more of the central scanner 28, the upper arm scanner 40, the lower arm scanner 42, the medial front scanner 68, the medial rear scanner 70, and/or the standalone scanners 110). Here, the structured light 3D imaging software may capture three to four camera images per 3D image. Such technology can calculate surface height dimensions comparability relatively easily. Other technologies may be used to obtain structured illumination using, e.g., technology similar to the XBox Kinect system to capture 3D position with a single image. Additionally, laser scanning may use the confocal method, which requires modulating the focal position and the lateral position of the laser beam. Here, the laser scanner captures a "slice" of the tooth and relies on translation of the probe to create the other dimension of the scan. Alternatively, 3D sensing may be accomplished using triangulation with a laser beam and imager to avoid needing to modulate the focal position. Stereoscopic imaging may deploy use of two cameras scanner (e.g., in one or more of the central scanner 28, the upper arm scanner 40, the lower arm scanner 42, the medial front scanner 68, the medial rear scanner 70, and/or the standalone scanners 110) and can typically provide depth information. Moreover, the dental imager 10 may also use interference methods to formulate a 3D model. Here, the position of the tooth may be measured using coherence, similar to optical coherence tomography. In another alternative embodiment, the dental imager 10 may use acoustic methods, similar to ultrasound, to obtain a 3D image of the intraoral cavity 18.

Here, position sensors based on acoustics may measure the relative size and shape of the teeth 16 by emitting a clicking sound that bounces off the relatively hard structure of the teeth 16. Such measurements may provide a single point or multi-point measurement. For example, the inputs can be extrapolated into a 3D profile using multiple input points and multiple microphones measuring sound waves bouncing off the teeth 16 during the scanning process.

Additionally, the features of the various embodiments disclosed herein may be mixed and/or matched as needed and/or desired. For example, different options for spacing the image/shape capturing elements (e.g., the scanners, cameras, ultrasound sensors, etc.) and the teeth 16 may include the central rounded guides 26, 26' and/or the lateral roller guides 36, 36' (e.g., made from rubber or the like) positioned on the upper inside portion of the arcuate lateral scanning arms 32, 32' (e.g., as shown in FIGS. 5 and 9-10), generally centrally located on the static head 88 (e.g., as shown in FIG. 5), or generally centrally located on the central platform 24 (e.g., as shown in FIGS. 9 and 10). In some embodiments, one or more of the central scanners 28 may be located between the central rounded guides 26, 26', such as shown with respect to FIG. 2. Other alternative embodiments may include use of the medial front scanner 68 and/or the medial rear scanner 70 with the arcuate front scanning arm 50, the arcuate rear scanning arm 52, and/or the respective angled stationary front or rear platforms 76, 78. Additionally, the lateral pads 94, 94' and/or the central pads 96, 96' (e.g., made from a Teflon material or the like) may be positioned on the upper boarder of the arcuate lateral scanning arms 32, 32' (e.g., as shown in FIGS. 6-8) and/or arcuate front scanning arm 50 and/or the arcuate rear scanning arm 52; on the center of the static head 88 (FIG. 6), on the center of the pivotable head 98 (FIG. 7), or on the center of the central platform 24 (FIG. 9). Here again, in some embodiments, one or more of the central scanners 28 may be located between the central pads 96, 96', such as in the position shown in FIG. 2 relative to the central rounded guides 26, 26'. Additionally, a front pad 106 and a rear pad 108 may be respectively mounted to the top portion of the angled stationary front platform 76 and the angled stationary rear platform 78 (e.g., as shown in FIGS. 5-9) or the front pad 106 and the rear pad 108 may mount directly to the static head 88 (e.g., as shown in FIG. 11) or directly to the central platform 24.

Additionally, each of the heads, i.e., the rotating head 22, the static head 88, and/or the pivotable head 98 may be exchangeable. Here, the respective head 22, 88, 98 may be configured for selective attachment and/or detachment from the neck region 86 such that the user can interchange the heads 22, 88, 98 for use with a single elongated handle 12. This feature may be potentially advantageous as it allow for replacement of the head (if broken) or use of a different head, depending on the desired use or task. To this end, use of a different head may be desired to obtain a different result, i.e., a head having specific scanning technology (e.g., laser scanners, cameras, ultrasound, etc.) may be used for different scanning circumstances, which may vary from patient to patient. For example, one such head may have scanning technology best suited to capture the shape/contour of the teeth 16 and convert that information into a 3D model. Subsequently, the head may be replaced with another one designed to more specifically capture color pictures of the teeth. Here, by use of an associated software system, the pictures could be converted into a 3D model; although, the head could simply be used to obtain detailed closed-up pictures of the teeth to identify potential issues. Thus, the dental imager 10 could have applications in both dentistry and/or orthodontics, as an example.

Although several embodiments have been described in detail for purposes of illustration, various modifications may be made without departing from the scope and spirit of the invention. Accordingly, the invention disclosed herein is not to be limited, except as by the appended claims.

What is claimed is:

1. A dental imager for imaging an intraoral cavity, comprising:
   a handle coupled to a head having a size and shape for select insertion into the intraoral cavity;
   a pair of lateral scanning arms coupled to the head or the handle and positioned opposite each other, each of the pair of lateral scanning arms including a top scanner and a bottom scanner associated therewith for imaging at least a portion of the intraoral cavity; and
   a guide having a size and shape for engagement with the intraoral cavity while simultaneously biasing the top scanner and the bottom scanner from the intraoral cavity as the dental imager moves relative to the intraoral cavity during imaging.

2. The dental imager of claim 1, including an activation sensor comprising an emitter in one of the pair of arcuate lateral scanning arms and a detector in the other of the pair of arcuate lateral scanning arms, the emitter and the detector being generally aligned such that a beam generated by the emitter is receivable by the detector during non-use and generally blocked by the intraoral cavity during use of the dental imager.

3. The dental imager of claim 1, wherein the guide comprises a pad having a surface permitting sliding movement over the intraoral cavity.

4. The dental imager of claim 3, including at least one central scanner mounted to the head or the handle and having a height relatively less than the pad.

5. The dental imager of claim 1, including a front medial scanning arm or a rear medial scanning arm coupled to the head or the handle.

6. The dental imager of claim 1, wherein the head or the handle includes a front angled platform carrying a front scanner and a rear angled platform carrying a rear scanner.

7. The dental imager of claim 6, wherein the guide comprises a front pad coupled to the front angled platform above the front scanner and a rear pad coupled to the rear angled platform above the rear scanner.

8. The dental imager of claim 1, including a communication circuit integral with the handle and in communication with at least one scanner for selectively transmitting imaging data of the intraoral cavity.

9. The dental imager of claim 8, wherein the communication circuit comprises a wireless transmitter, a USB connector, or a fiber optic connector.

10. The dental imager of claim 1, wherein at least one scanner is selected from the group consisting of a time of flight (ToF) scanner, a stereoscopic vision scanner, a light field moment imaging scanner, a fixed structured light scanner, a programmable structured light (DLP) scanner, a 3D or 4D ultrasound scanner, a digital camera scanner, a light emitting diode (LED) scanner, and a laser scanner.

11. The dental imager of claim 1, wherein the head is detachable from the handle.

12. The dental imager of claim 1, including a front pad and a rear pad mounted to the head, wherein the pair of lateral scanning arms are static scanning arms and immovably coupled to the head or the handle.

13. A dental imager for imaging an intraoral cavity, comprising:
a handle coupled to a head having a size and shape for select insertion into the intraoral cavity;
a pair of arcuate lateral scanning arms coupled to the head or the handle and positioned opposite one other, each of the pair of arcuate lateral scanning arms having a scanner associated therewith for imaging at least a portion of the intraoral cavity;
an activation sensor comprising an emitter in one of the pair of arcuate lateral scanning arms and a detector in the other of the pair of arcuate lateral scanning arms, the emitter and the detector being generally aligned such that a beam generated by the emitter is receivable by the detector during non-use and generally blocked by the intraoral cavity during use of the dental imager; and
a guide having a size and shape for engagement with the intraoral cavity while simultaneously substantially biasing the scanner from the intraoral cavity as the dental imager moves relative to the intraoral cavity during imaging.

14. The dental imager of claim 13, including a top scanner or a bottom scanner mounted to each of the pair of arcuate lateral scanning arms.

15. The dental imager of claim 13, wherein the guide comprises a pad having a surface permitting sliding movement over the intraoral cavity.

16. The dental imager of claim 15, including at least one central scanner mounted to the head and having a height relatively less than the pad.

17. The dental imager of claim 13, wherein the head includes a front angled platform carrying a front scanner and a rear angled platform carrying a rear scanner.

18. The dental imager of claim 13, including a communication circuit integral with the head or the handle and in communication with at least one scanner for selectively transmitting imaging data of the intraoral cavity.

19. The dental imager of claim 13, wherein at least one scanner is selected from the group consisting of a time of flight (ToF) scanner, a stereoscopic vision scanner, a light field moment imaging scanner, a fixed structured light scanner, a programmable structured light (DLP) scanner, a 3D or 4D ultrasound scanner, a digital camera scanner, a light emitting diode (LED) scanner, and a laser scanner.

20. The dental imager of claim 13, including a front pad and a rear pad mounted to the head or the handle, wherein the pair of arcuate lateral scanning arms are immovably coupled to the head.

21. A dental imager for imaging an intraoral cavity, comprising:
a handle coupled to a head having a size and shape for select insertion into the intraoral cavity;
a front medial scanning arm or a rear medial scanning arm coupled to the head or the handle;
at least one lateral scanning arm projecting outwardly from the head or the handle and having a scanner associated therewith for imaging at least a portion of the intraoral cavity; and
a guide having a size and shape for engagement with the intraoral cavity while simultaneously substantially biasing the scanner from the intraoral cavity as the dental imager moves relative to the intraoral cavity during imaging.

22. The dental imager of claim 21, wherein the at least one lateral scanning arm comprises a pair of arcuate lateral scanning arms statically coupled to the head or the handle opposite each other.

23. The dental imager of claim 21, including at least one central scanner mounted to the head and having a height relatively less than the guide.

24. The dental imager of claim 21, wherein the head or the handle includes a front angled platform carrying a front scanner and a rear angled platform carrying a rear scanner.

25. The dental imager of claim 24, wherein the guide comprises a front pad coupled to the front angled platform above the front scanner and a rear pad coupled to the rear angled platform above the rear scanner.

26. The dental imager of claim 21, including a communication circuit integral with the head or the handle and in communication with the scanner for selectively transmitting imaging data of the intraoral cavity.

27. The dental imager of claim 21, wherein the scanner is selected from the group consisting of a time of flight (ToF) scanner, a stereoscopic vision scanner, a light field moment imaging scanner, a fixed structured light scanner, a programmable structured light (DLP) scanner, a 3D or 4D ultrasound scanner, a digital camera scanner, a light emitting diode (LED) scanner, and a laser scanner.

28. A dental imager for imaging an intraoral cavity, comprising:
a handle having a proximal end and a distal end;
a head coupled to the handle and having a size and shape for select insertion into the intraoral cavity;
a pair of static scanning arms immovably coupled to the head or the handle, wherein each static scanning arm of the pair of static scanning arms has a scanner associated therewith for imaging at least a portion of the intraoral cavity;
a front pad and a rear pad mounted to the head or the handle; and
a guide having a size and shape for engagement with the intraoral cavity while simultaneously substantially biasing the scanner from the intraoral cavity as the dental imager moves relative to the intraoral cavity during imaging.

29. The dental imager of claim 28, including at least one central scanner mounted to the head or the handle and having a height relatively less than the guide.

30. The dental imager of claim 28, including a communication circuit integral with the head or the handle and in communication with at least one scanner for selectively transmitting imaging data of the intraoral cavity.

31. The dental imager of claim 28, wherein at least one scanner is selected from the group consisting of a time of flight (ToF) scanner, a stereoscopic vision scanner, a light field moment imaging scanner, a fixed structured light scanner, a programmable structured light (DLP) scanner, a 3D or 4D ultrasound scanner, a digital camera scanner, a light emitting diode (LED) scanner, and a laser scanner.

* * * * *